US012694775B2

(12) United States Patent
 Beyer

(10) Patent No.: US 12,694,775 B2
(45) Date of Patent: Jul. 28, 2026

(54) AED PROMPTED PSAP NOTIFICATIONS

(71) Applicant: Avive Solutions, Inc., Brisbane, CA (US)

(72) Inventor: Rory M. Beyer, San Mateo, CA (US)

(73) Assignee: Avive Solutions, Inc., Brisbane, CA (US)

( * ) Notice: Subject to any disclaimer, the term of this patent is extended or adjusted under 35 U.S.C. 154(b) by 30 days.

(21) Appl. No.: 18/940,214

(22) Filed: Nov. 7, 2024

(65) Prior Publication Data

US 2025/0061790 A1     Feb. 20, 2025

Related U.S. Application Data

(63) Continuation-in-part of application No. 18/653,267, filed on May 2, 2024, and a continuation-in-part of application No. 18/653,270, filed on May 2, 2024, and a continuation-in-part of application No. 18/653,274, filed on May 2, 2024, now Pat. No. (Continued)

(51) Int. Cl.
| | |
|---|---|
| *G08B 21/02* | (2006.01) |
| *G08B 25/00* | (2006.01) |
| *G08B 25/14* | (2006.01) |
| *G08B 27/00* | (2006.01) |
| *H04W 4/16* | (2009.01) |
| *H04W 4/90* | (2018.01) |
| *A61N 1/39* | (2006.01) |
| *H04W 4/02* | (2018.01) |

(52) U.S. Cl.
CPC ........... *G08B 21/02* (2013.01); *G08B 25/006* (2013.01); *G08B 25/14* (2013.01); *G08B*

*27/001* (2013.01); *H04W 4/16* (2013.01); *H04W 4/90* (2018.02); *A61N 1/3904* (2017.08); *H04W 4/02* (2013.01)

(58) Field of Classification Search
CPC ...................................................... G08B 21/02
USPC ....................................................... 340/573.1
See application file for complete search history.

(56) References Cited

U.S. PATENT DOCUMENTS

| | | |
|---|---|---|
| 10,112,054 B2 | 10/2018 | Beyer et al. |
| 10,993,626 B2 | 5/2021 | Elghazzawi et al. |

(Continued)

OTHER PUBLICATIONS

Bongberg et al., U.S. Appl. No. 17/217,738, filed Mar. 30, 2021.

*Primary Examiner* — Travis R Hunnings
(74) *Attorney, Agent, or Firm* — Beyer Law Group LLP

(57) ABSTRACT

Systems and processes are described that facilitate notifying PSAPs and others of emergency uses of AEDs. An AED management server receives electronic messages from the AEDs during emergency use of such AED. The server determines whether an emergency services triggering event has occurred based on various factors. When a triggering event has occurred, an incident notification is sent that directly or indirectly causes a PSAP responsible for handling medical incidents in a region that includes the reporting AED to be notified of the emergency use. Factors included in determining whether an incident notification is to be sent may include factors such as the state of the AED, the perceived accuracy of a reported location of the AED, whether PSAP notifications are enabled, etc. In some embodiments contact notifications are also enabled and/or an AED administrator may set various preferences related to incident notification for their AEDs.

21 Claims, 6 Drawing Sheets

Related U.S. Application Data 12,594,431, and a continuation-in-part of application No. 18/521,405, filed on Nov. 28, 2023, now Pat. No. 12,211,368, which is a continuation of application No. 17/501,900, filed on Oct. 14, 2021, now Pat. No. 11,869,338.

(60) Provisional application No. 63/685,485, filed on Aug. 21, 2024, provisional application No. 63/093,568, filed on Oct. 19, 2020.

(56) References Cited

U.S. PATENT DOCUMENTS

| | | | |
|---|---|---|---|
| 11,210,919 | B2 | 12/2021 | Beyer et al. |
| 11,266,826 | B2 | 3/2022 | Andrews |
| 11,331,471 | B2 | 5/2022 | Andrews et al. |
| 11,640,755 | B2 | 5/2023 | Beyer et al. |
| 11,691,021 | B2 | 7/2023 | Andrews et al. |
| 11,869,338 | B1 | 1/2024 | Beyer et al. |
| 11,908,299 | B2 | 2/2024 | Beyer et al. |
| 12,020,548 | B2 | 6/2024 | Jafri et al. |
| 12,106,650 | B2 | 10/2024 | Beyer et al. |
| 12,150,026 | B2 | 11/2024 | Barash et al. |
| 2004/0055828 | A1* | 3/2004 | Kavounas ............. B66B 1/2408 187/306 |
| 2007/0299473 | A1* | 12/2007 | Matos .................. A61N 1/3904 607/9 |
| 2009/0284378 | A1* | 11/2009 | Ferren .................... G08B 21/06 340/573.1 |
| 2010/0286490 | A1* | 11/2010 | Koverzin ........... G08B 21/0492 704/231 |
| 2011/0060378 | A1* | 3/2011 | Tuysserkani ......... A61B 5/0022 370/352 |
| 2011/0071880 | A1* | 3/2011 | Spector ................. H04W 76/50 340/539.13 |
| 2011/0152702 | A1* | 6/2011 | Goto ...................... G08B 21/02 340/7.58 |
| 2014/0266718 | A1 | 9/2014 | Bongberg et al. |
| 2015/0206408 | A1* | 7/2015 | LaLonde .............. A61B 5/0026 340/539.12 |
| 2015/0343229 | A1* | 12/2015 | Peterson ................ G16Z 99/00 607/6 |
| 2016/0140834 | A1* | 5/2016 | Tran ..................... A61B 5/0022 340/539.11 |
| 2022/0241600 | A1 | 8/2022 | Andrews et al. |
| 2024/0096203 | A1 | 3/2024 | Beyer et al. |
| 2024/0144802 | A1 | 5/2024 | Beyer et al. |
| 2024/0366953 | A1 | 11/2024 | Beyer et al. |
| 2024/0371511 | A1 | 11/2024 | Beyer et al. |
| 2024/0371512 | A1 | 11/2024 | Beyer et al. |

* cited by examiner

AED PROMPTED PSAP NOTIFICATIONS

CROSS-REFERENCE TO RELATED APPLICATIONS

This application claims priority of U.S. Provisional Application No. 63/685,485, filed Aug. 21, 2024 (P031P), which is incorporated by reference in its entirety.

This application is also a Continuation-in-Part of U.S. patent application Ser. No. 18/653,267, filed May 2, 2024 (P027A); Ser. No. 18/653,270, filed May 2, 2024 (P027B); and Ser. No. 18/653,274, filed May 2, 2024 (P027C); each of which is incorporated herein by reference in its entirety.

This application is also a Continuation in Part of U.S. application Ser. No. 18/521,405, filed on Nov. 28, 2023 (P023C1), (now U.S. Pat. No. 12,211,368, issued Jan. 28, 2025), which is a Continuation of U.S. application Ser. No. 17/501,900, filed on Oct. 14, 2021 (now U.S. Pat. No. 11,869,338, issued Jan. 9, 2024) (P023), which claims priority of U.S. Provisional Application No. 63/093,568, filed on Oct. 19, 2020 (P023P), all of which are incorporated by reference herein in their entirety.

FIELD

The present disclosure relates generally to automated external defibrillators (AEDs) and defibrillator management systems configured to notify public safety answering points (PSAPs) and/or other interested parties of the use of such AEDs.

BACKGROUND

Sudden cardiac arrest is one of the leading causes of death. In the United States alone, roughly 350,000 people die each year from sudden cardiac arrest. It is the leading cause of death for individuals over 40 and the #1 killer of student athletes. The most effective treatment for sudden cardiac arrest is the use of CPR coupled with defibrillation. Automated external defibrillators (AEDs) are portable devices designed to automatically check for life-threatening heart rhythms associated with sudden cardiac arrest and to send an electrical shock to the heart to try to restore a normal rhythm when shockable heart rhythms are detected. The two most common conditions treated by AEDs are Pulseless Ventricular tachycardia (aka VT or V-Tach) and Ventricular fibrillation (VF or V-Fib). AEDs are typically designed so that they can be used by a lay person in situations where professional medical help is not available.

Given their potential to save lives, automated external defibrillators have been deployed in a relatively wide variety of public and private locations so that they are available in the event that a person in the vicinity goes into cardiac arrest. By way of example, AEDs may be found in corporate and government offices, shopping centers, airports, airplanes, restaurants, casinos, hotels, sports stadiums, schools, fitness centers and a variety of other locations where people may congregate.

When a cardiac arrest occurs in out-of-hospital settings, witnesses are typically encouraged to call emergency ser-vices—e.g., a public safety answering point (PSAP) such as 911 in the United States. In parallel witnesses are encour-aged to begin cardiopulmonary resuscitation (CPR) and deploy an AED if an AED is available. For many years there have been proposals to provide AEDs that are configured to automatically call a PSAP (e.g., initiate a voice phone call to 911) to notify the PSAP of a potential cardiac arrest incident when an AED is used. However, the current inventors are unaware of any commercially available defibrillators that are designed to place such calls or to otherwise initiate com-munications with a PSAP when the AED is used. Although existing AEDs and emergency response systems work well, it would be desirable to provide AEDs and associated systems that have the ability to reliably and automatically notify the appropriate PSAP and/or other interested parties of the existence of a medical emergency when such AEDs are deployed.

SUMMARY

A variety of systems and processes are described that facilitate notifying an emergency service call center (e.g., a Public Safety Answering Point (PSAP)) of a potential car-diac arrest incident. In one aspect, a server is arranged to receive one or more electronic messages from the AED during emergency use of the AED. The server determines that an emergency services triggering event has occurred based at least in part on the reception of reception of a first message that directly or indirectly indicates one of the following has occurred: (i) that the AED has detected placement of the AED's electrode pads on a patient, (ii) that the AED has performed a classification of a heart rhythm of the patient, and (iii) that the AED has determined that the patient has a shockable heart rhythm. In response to deter-mining that an emergency services notification triggering event has occurred, the server sends an electronic incident notification message that either directly or indirectly causes an emergency services call center responsible for handling medical incidents in a region that includes the location of the AED to be notified of the emergency use of the AED. The incident notification message includes an incident location indicative of the location of the AED and is sent in real time during emergency use of the AED.

In another aspect, a server receives a first electronic message from an automated external defibrillator (AED) during emergency use of the AED that informs the server that the AED is currently in use. The server also receives an indication of the AED's current location together with a location accuracy measure or location accuracy confidence value. The location accuracy measure or location accuracy confidence value is received during the emergency use of the AED either in the first electronic message or a second electronic message from the AED. The server determines whether the location of the AED is known within a desig-nated location precision threshold based at least in part on the received location accuracy measure or location accuracy confidence value. The server then determines whether an emergency services notification triggering event has occurred based at least in part on: (a) the reception of the first message, and (b) the determination that the location of the AED is known within the designated location precision threshold. When an emergency services notification trigger-ing event has occurred, the server sends an electronic incident notification message that directly or indirectly causes an emergency services call center responsible for handling medical incidents in a region that includes the location of the AED to be notified of the emergency use of the AED. The incident notification message includes an incident location indicative of the location of the AED. The server is located remotely relative to both the AED and the emergency services call center, and the electronic incident notification message is sent in real time during the emer-gency use of the AED.

The server is preferably configured to receive electronic messages from a multiplicity of AEDs and the server determines whether an emergency services notification triggering event has occurred for each incident for which the server receives an electronic message. Each time an emergency services notification triggering event has occurred, the server sends a corresponding electronic incident notification message to facilitate notification of the appropriate emergency services call center.

In some embodiments, the determination that a triggering event has occurred is based in part on the first message indicating one selected from the group consisting of (i) that the AED has detected placement of the AED's electrode pads on a patient, (ii) that the AED has performed a classification of a heart rhythm of the patient, and (iii) that the AED has determined that the patient has a shockable heart rhythm as discussed with respect to the first aspect.

In some embodiments, the first message indicates that the AED has detected placement of the AED's electrode pads on the patient whereby the determination that the emergency services notification triggering event has occurred is based at least in part on the reception of the first message indicating that the AED has detected placement of the AED's electrode pads on a patient.

In other embodiments, the first message indicates that the AED has performed a classification of a heart rhythm of the patient whereby the determination that the emergency services notification triggering event has occurred is based at least in part on the reception of the first message indicating that the AED has performed a classification of a heart rhythm of the patient.

In still other embodiments, the first message indicates that the AED has determined that the patient has a shockable heart rhythm whereby the determination that the emergency services notification triggering event has occurred is based at least in part on the reception of the first message indicating that the AED has determined that the patient has a shockable heart rhythm.

In some embodiments, the incident notification message is sent directly from the server to a computer aided dispatch system used by the emergency services call center.

In other embodiments, the incident notification message is sent to an emergency services interface that automatically sends a call center incident notification to a computer aided dispatch system used by the emergency services call center.

In some embodiments, when the server determines that the location of a notifying AED is not known within the designated location precision threshold, no electronic incident notification message is sent for that incident unless/until the location of the incident is known within the designated location precision threshold.

In many embodiments, the emergency services call center takes the form of a public safety answering point (PSAP).

In another aspect, the server determines that a contact notification triggering event has occurred based at least in part on the reception of a first message and that an emergency services notification triggering event has occurred based at least in part on the reception of the first message or a second message that has at least some different content than the first message. In response to determining that the contact notification triggering event has occurred, the server sends a first electronic incident notification to one or more pre-designated notification targets that are associated with the AED. In response to determining that an emergency services notification triggering event has occurred, an electronic second incident notification message is sent that causes an emergency services call center responsible for handling medical incidents in a region that includes the location of the AED to be notified of the emergency use of the AED. The second incident notification message includes an incident location indicative of the location of the AED. The first and second electronic incident notification messages are sent to different notification targets during the emergency use of the AED and are transmitted in response to different triggering events and respectively constitute initial communications sent to their respective notification targets notifying such notification targets of the emergency use of the AED.

In some embodiments the emergency services triggering event determination is based at least in part on whether one of the first or second messages indicating one selected from the group consisting of (i) that the AED has detected placement of the AED's electrode pads on a patient or that the AED, (ii) that the AED has performed a classification of a heart rhythm of the patient, and (iii) that the AED has determined that the patient has a shockable heart rhythm.

In some embodiments, at least one of the first or second messages includes an indication of the AED's location together with a location accuracy measure or location accuracy confidence value. The server, determines whether the location of the AED is known within a designated location precision threshold based at least in part on the received location accuracy measure or location accuracy confidence value. The second electronic incident notification is only sent by the server when the server determines that the location of the AED is known within the designated location precision threshold.

In some embodiments, the contact notification(s) is/are sent to one or more contacts designated by an administrator or manager of the AED.

In some embodiments, the contact notification triggering event is selected from the group consisting of activation of the AED, or accessing the electrode pads.

In another aspect, a server electronically receives an emergency services notifications settings command from a management platform user interface rendered on a computing device associated with an administrator associated with a first automated external defibrillator (AED). The emergency services notifications settings command indicates whether emergency uses of the AED should be reported to emergency services in real-time during emergency use of the AED. In response to reception of the emergency services notifications command, the server causes a record in a first database associated with the server to be marked to indicate whether emergency services notifications are enabled or disabled for the AED. A first electronic message is received from an AED that directly or indirectly indicates that that the AED is currently in emergency use. The server also receives an indication of the AED's location together with a location accuracy measure or location accuracy confidence value. The location accuracy measure or location accuracy confidence value is received in during the emergency use of the AED either in the first electronic message or a second electronic message from the AED. The server determining whether the location of the AED is known within a designated location precision threshold based at least in part on the received location accuracy measure or location accuracy confidence value. The server also determines whether an emergency services notification triggering event has occurred based at least in part on (a) whether emergency services notifications are enabled for the AED, (b) the reception of the first message, and (c) the determination that the location of the AED is known within the designated location precision threshold. In response to determining that an emergency services notification triggering event has occurred, an electronic incident notification message is sent that causes an emergency services call center responsible for handling medical incidents in a region that includes the location of the AED to be notified of the emergency use of the AED. The incident notification message includes an incident location indicative of the location of the AED. Generally, the server is located remotely relative to both the AED and the emergency services call center, and the electronic incident notification message is sent during the emergency use of the AED.

In some embodiments, when emergency services notifications are disabled for the AED it is determined that an emergency services notification triggering event has not occurred and no electronic incident notification message is sent in response to reception of the first message.

In some embodiments, when it is determined that the location of the AED is not known within the designated location precision threshold, it is determined that an emergency services notification triggering event has not occurred and no electronic incident notification message is sent in response to reception of the first message.

In some embodiments, the first message indicates that the AED has detected placement of the AED's electrode pads on the patient whereby the determination that the emergency services notification triggering event has occurred is based at least in part on the reception of the first message indicating that the AED has detected placement of the AED's electrode pads on a patient.

In some embodiments, the first message indicates that the AED has performed a classification of a heart rhythm of the patient whereby the determination that the emergency services notification triggering event has occurred is based at least in part on the reception of the first message indicating that the AED has performed a classification of a heart rhythm of the patient.

In some embodiments, the first message indicates that the AED has determined that the patient has a shockable heart rhythm whereby the determination that the emergency services notification triggering event has occurred is based at least in part on the reception of the first message indicating that the AED has determined that the patient has a shockable heart rhythm.

In another aspect, a server electronically receives an emergency services notifications settings command from a management platform user interface rendered on a computing device associated with an administrator associated with a first automated external defibrillator (AED. The emergency services notifications settings command indicates whether emergency uses of the AED should be reported to emergency services in real-time during emergency use of the AED. In response to reception of the emergency services notifications command, a record in a first database associated with the server is marked to indicate whether emergency services notifications are enabled or disabled for the AED. The server receives messages from an AED in real-time during an emergency use of the AED. The server determines whether an emergency services notification triggering event has occurred based at least in part on (a) whether emergency services notifications are enabled for the AED and (b) the reception of the first message. In response to determining that an emergency services notification triggering event has occurred, sending an electronic incident notification message is sent that directly or indirectly causes an emergency services call center responsible for handling medical incidents in a region that includes the location of the AED to be notified of the emergency use of the AED. The incident notification message includes an incident location indicative of the location of the AED.

BRIEF DESCRIPTION OF THE DRAWINGS

The invention and the advantages thereof, may best be understood by reference to the following description taken in conjunction with the accompanying drawings in which.

In the drawings, like reference numerals are sometimes used to designate like structural elements. It should also be appreciated that the depictions in the figures are diagrammatic and not to scale.

DETAILED DESCRIPTION

The present invention relates generally to systems for notifying Public Safety Answering Points (PSAPs) and/or other relevant parties of the deployment of an AED.

Figure 1:
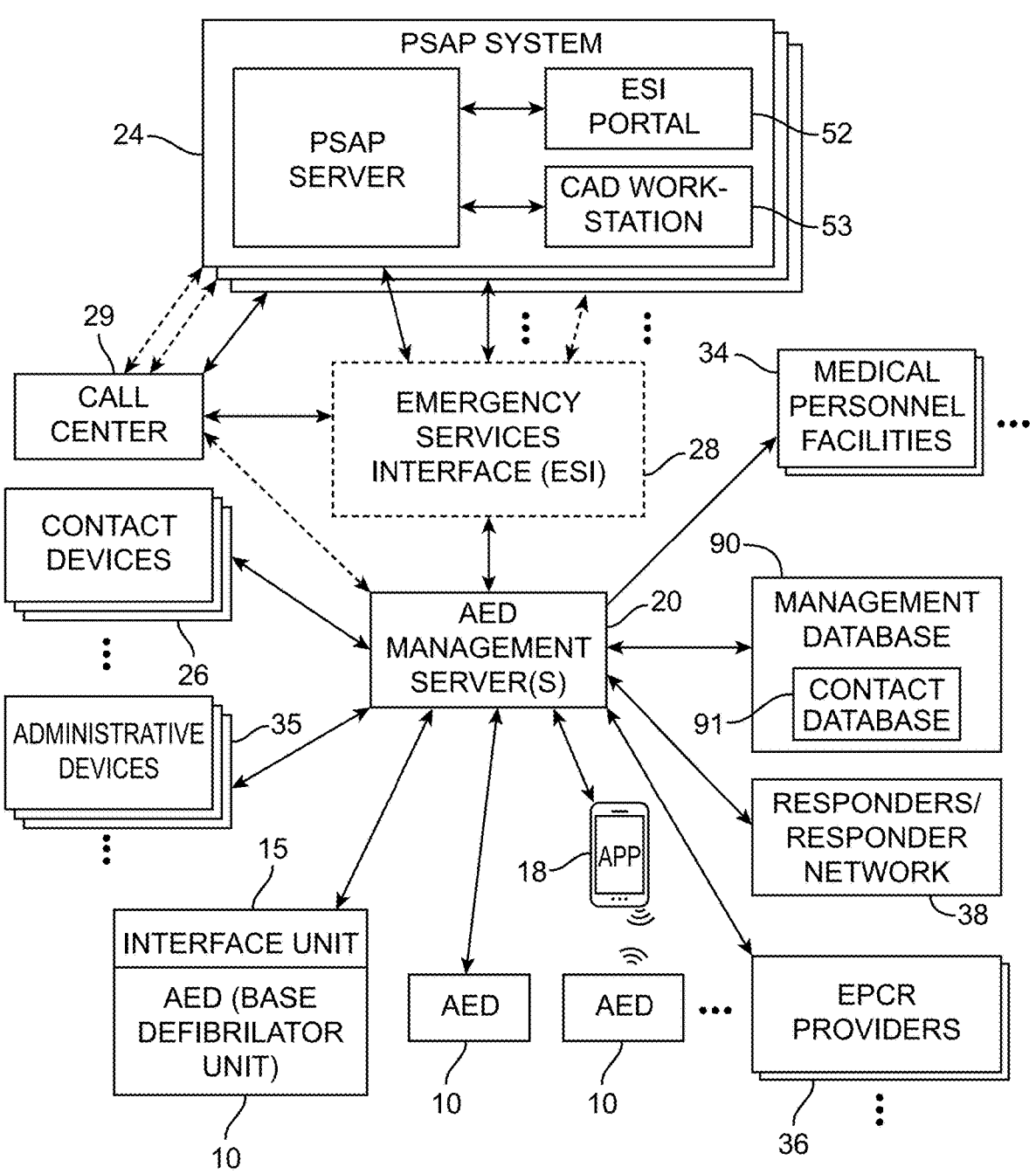
FIG. 1 diagrammatically illustrates a system architecture in accordance with one embodiment.

FIG. 1 diagrammatically illustrates a representative system architecture. The system includes an AED management server infrastructure 20 (often simply referred to as the management server or as an AED network server) that is configured to bidirectionally communicate with a multiplicity of connected AEDs 10. The management server 20 also bidirectionally communicates directly or indirectly with a multiplicity of emergency call centers/Public Safety Answering Points (PSAPs) 24 (e.g., 911 call centers in the U.S. and Canada, 112 call centers in Europe, 999 call centers in some jurisdictions and other such emergency services call centers). The management server further communicates with a number of contact devices 26, which are computing devices (e.g., smartphones, tablets, computers, etc.) associated with people that the AED's administrator(s) have indicated should be contacted if/when the AED is used. In the illustrated embodiment, the AED management server infrastructure 20 also serves as a management platform server. As such, it can also be accessed by a variety of computing devices 30 (sometimes referred to as administrator computing devices) that AED owners, administrators and other interested parties can utilize to manage their AEDs.

The management server 20 is also configured to communicate with a variety of other systems and devices to provide relevant AED information, as for example, medical personnel or facilities 34 (e.g., doctors, emergency medical technicians, hospitals, etc.), electronic patient care records (EPCR) providers 36, responder networks 38 (or volunteer responders if the management server serves as the responder network server), and other entities/systems. Although responder network 38 is shown as a separate entity in FIG. 1, in many embodiments, the AED management server infrastructure 20 also serves as an AED inclusive responder network server.

In the illustrated embodiment, the management server is shown as a single box. It should be appreciated that the functionality of the management server infrastructure can be performed by a single physical and/or virtual server, or any number of physical and/or virtual machines working alone, together or in parallel to perform the various described tasks. As such, the terms server and/or management server should be understood to include one or more physical and/or virtual servers that cooperate to handle the described tasks.

Each physical server includes a processing unit composed of one or more processors and memory. The memory may include local, remote, dedicated and/or shared physical memory and/or caches which may be of any suitable form. The server has software (programmed instructions) stored in the associated memory that when executed by the processor cause the server to perform the described server functionalities.

In the embodiment illustrated in FIG. 1, the AED management server 20 is configured to electronically communicate with the PSAPs 24 by way of an optional emergency services interface (ESI) 28. In other embodiments, the AED network server 20 electronically communicates with the PSAPs directly or with some PSAPs directly and others via one or more ESIs. Currently, some PSAPs are unable or unwilling to accept electronic notifications from devices and can therefore only be contacted via voice call. In such cases the management server can initiate an EMS response by sending an electronic notification to a call center 29 which, in turn, places a voice call to the appropriate PSAP to inform the PSAP of the incident. In some embodiments, the ESI 28 may include a/the call center 29 for communicating with PSAPs that are unable or unwilling to accept electronic notifications.

By way of background PSAPs were originally designed to handle voice calls (e.g., 911 calls), but were not well suited to receive data from external sources that might be relevant to such calls. As the availability of data relevant to emergency incidents increased, emergency services interfaces were developed that helped route data (including, but not limited to device data) that is relevant to a particular incident to the correct PSAP and to provide mechanisms for associating such data with the correct voice call(s) reporting an incident. In general, ESIs have the ability to receive data relevant to an emergency incident, determine the appropriate PSAP to handle that incident based on the location of the incident, and deliver the relevant data to the appropriate PSAP in a manner that can be utilized by a telecommunicator that is handling a voice call.

Telecommunicators within a PSAP will frequently have access to an ESI portal that allows them to receive data relevant to various emergency calls. This may take the form of a dedicated ESI screen, an ESI frame or window rendered on another screen of the computer aided dispatch (CAD) system or in other suitable presentations. In such systems, the telecommunicator is able to view data associated with a voice call in the ESI portal. In some circumstances, the ESI serves as a clearinghouse for data supplied to the PSAP. That is, the ESI may take data from one or more distinct sources, process such data appropriately and display the relevant information on the telecommunicator's ESI portal.

In the United States, RapidSOS is currently the largest emergency services interface and is well suited for such applications. One particularly desirable feature of RapidSOS is that they currently have relationships with a large percentage of the emergency call centers in the United States and are already set up to send data received from other sources, including data from other connected devices (not defibrillators) to the call centers. Although RapidSOS is mentioned specifically, it should be appreciated that the same approach can be used with any or with multiple different ESIs as appropriate.

The ESI 28 is configured to communicate with a number of (and potentially a large number of) PSAPs 30. The ESI can use location data forwarded by the AED network server to determine the appropriate PSAP 24 to handle any particular incident. As discussed above, the PSAP's CAD system or an ESI portal 52 which is associated with (i.e., effectively a part of) the CAD system is designed to receive data relating to incidents from the ESI 28.

In some embodiments, the functionality of the ESI 28 may be integrated into the AED network server 20 (or vice versa). Such an architecture is substantially similar to the architecture discussed above with respect to FIG. 1 except that the AED management server 20 itself determines the appropriate PSAP for any particular incident based on the incident location reported by the AED (and any other relevant factors). The AED network server then communicates directly with the selected PSAP thereby eliminating the need for a separate ESI.

The various nodes illustrated in FIG. 1 (e.g., the AEDs 10, the management server 20, the PSAPs 24, the contact devices 26, the ESI 28, the call center 29, the administrator computing devices 30) can communicate via any suitable communications network, as for example, a global communications network (e.g., the Internet) or other suitable communication networks. In some embodiments, the AEDs 10 include Wi-Fi, cellular and Bluetooth capabilities to facilitate communications with the management server 20 via a variety of paths. This helps ensure that the AEDs can communicate with the management server most any time, including both when they are in a standby mode and when they are being used to treat a potential cardiac arrest victim. In some circumstances, an AED 10 may communicate with the management server by way of an intermediary such as a stand (e.g., a charging stand) or a passing smartphone as diagrammatically represented by the combination of AED 10 and phone 18 in FIG. 1.

The applicant has also described a number of AED inclusive responder networks, responder network integrations, EPCR integrations and AED management platforms. By way of example, U.S. Pat. No. 10,580,280 (P014B); U.S. Pat. No. 10,565,845 (P014A); U.S. Pat. No. 10,957,178 (P014X1); U.S. Pat. No. 11,138,855 (P014AX2); U.S. Pat. No. 11,210,020 (P021); U.S. Pat. No. 11,645,899 (P014X3); U.S. Pat. No. 11,640,755 (P021X1); U.S. Pat. No. 11,869, 338 (P023) and U.S. patent application Ser. No. 17/100,154 (now U.S. Publication No. 2021/153817) (P020A); Ser. No. 17/100,313 (now U.S. Publication No. 2021/0154487) (P020B); Ser. No. 17/217,738 (P022); Ser. No. 17/903,642 (now U.S. Publication No. 2023/0008570) (P025); Ser. No. 18/653,267 (P027A) and Ser. No. 18/653,274 (P027B), each of which are incorporated herein by reference, describe a few such systems and integrations.

AED Reported Current Status Information

The AEDs 10 are configured to send status messages directly or indirectly to the management server 20 at regular intervals. Preferably the status messages are sent on the scale of at least once a day or more frequently when in the standby mode and on the scale of every few seconds or more frequently during emergency use. There are a number of pathways by which the status messages may be sent from the AED to the management server. As suggested above, in various embodiments, the AEDs may have cellular, Wi-Fi, Bluetooth, satellite and/or other communications capabilities to facilitate communications with AED management server via appropriate networks, including global communications networks, Wi-Fi networks, cellular networks, satellite-based networks, etc. A variety of different communications protocols can be utilized in connection with the different networks. For example, WebSockets, Server-Sent Events (SSE), MQTT, short polling, long polling and a variety of other suitable techniques can be used. In some embodiments, the AEDs transmit status messages to intermediary devices via short range wireless technologies such as Bluetooth Low Energy (BLE) advertisements. Status messages received by an intermediary device are then forwarded to the management server. The intermediary devices may take a wide variety of forms, as for example, Smartphones, modular interface units such as those described in some of the incorporated patents, or connected stands, other base stations, tablets, etc. There are a number of protocols that can be used for various Wi-Fi, cellular or Bluetooth communications, including, for example, web sockets, server-sent events, MQTT, short and long polling, etc.

In some implementations, the AED may be modular in nature in that it includes a fully functional base AED unit with an attached interface unit that is not required for the base unit to independently function as an automated external defibrillator. In some embodiments, the interface unit includes a display (which may be a touch screen display) and at least some of the aforementioned communications capabilities (e.g., Wi-Fi, cellular, satellite capabilities). In some embodiments, the interface unit is independently powered relative to the base defibrillator unit. In some embodiments, the interface unit also provides location determining services, which may be based on any of a variety of technologies including Global Navigation Satellite Systems (GNSS) (e.g., GPS), Wi-Fi positioning, cellular triangulation, assisted GPS, Bluetooth Beacons, Near-Field Communications (NFC) and/or other location determining technologies. The interface unit includes one or more processors that controls the display and other functionality such that in appropriate circumstances, the interface unit can provide communication services and display content without necessarily even waking up the base defibrillator unit. For the purpose of this discussion, these types of interface units are considered a part of the AED. However, the modular nature of the defibrillator system provides a number of advantages that can be useful.

When such an interface unit is used, the interface unit receives status messages from the base defibrillator unit and then forwards the status message to the AED management server via any of the aforementioned routes. In some circumstances an attached interface unit (or a different intermediate unit located close to the AED) may add other relevant information known by the intermediate unit that is useful for the server, as for example the current location of the AED, environmental information such as a measured temperature and/or other sensed information. The location information may include the geolocation including the latitude and longitude coordinates and the altitude/elevation of the AED. The location information may also include location accuracy information such as the Circular Error Probability (CEP) or other measures of the perceived accuracy of the location information. The measured temperature may be a sensed temperature of the device, the ambient temperature, or any other temperature that the interface unit is capable of measuring. Other sensed information may include accelerometer data and/or any medical information that the interface unit is capable of detecting (e.g., blood oxygen levels, ECG measurements, respiration related measurements, audio and/or video from the incident scene etc.). Audio and/or video from the incident can be progressively conveyed "live" to the appropriate PSAP by way of the management server 20 using a "store and stream" messaging approach as described, for example, in U.S. Pat. No. 10,158, 591 which is incorporated herein by reference.

In some embodiments, the interface unit may also report its own status information. Examples of interface unit status information include, the battery charge level of the interface unit battery, a power mode that the interface unit is in (which may be indicative of whether eDRX is enabled and/or how often the unit checks for messages), the an indication of whether the interface unit is currently plugged into a power supply and/or what type of power supply it is connected to, the results of the most recent self-test of the interface unit, whether a screensaver mode is enabled, which training mode is set for the AED, whether each of location services, Bluetooth services, Wi-Fi services and cellular services are enabled or disabled, the interface unit serial number, the interface unit SIM card #, the interface unit software version number, the interface unit FCC ID number(s), the most recent screen state (e.g. what is or has most recently been displayed on the display screen), an interface unit power-on reason (e.g., the device woke up due to an interface unit button press or due to an AED activation, etc.), error codes, log files, etc. It can also include the connection type that is being used (e.g., a cellular or Wi-Fi network, etc.), the MAC address of the interface unit. The interface unit can also report general device information such as whether a base unit's Bluetooth capability is enabled, the power mode that the interface unit is currently (including charge pack mode).

A few representative status message transmission approaches are described in more detail in some of the incorporated patents and patent application, including, for example U.S. Pat. No. 10,773,091 (P006E); U.S. Pat. No. 11,077,312 (P016B); U.S. Pat. No. 11,210,020 (P021) and U.S. Pat. No. 11,640,755 (P021X1).

The frequency of status message updates may vary based on the systems needs and capabilities of the AEDs involved, but in general, updates of at least once a day and any time the AED determines that a material change has occurred are preferred. In some embodiments and/or circumstances, the updates may be sent substantially continuously (e.g., every few seconds or less) particularly when the AED is in use, or its location or circumstances are changing. By way of example, when the AED is known to be moving in a circumstance where it is on its way to an emergency incident, status update frequencies on the order of every 1 to 10 seconds are believed to work well. Similarly, when the AED is in use during an emergency, update frequencies on the order of every 1 to 10 seconds are believed to work well. In another example, in circumstances where the AED is broadcasting status messages to any nearby listening devices via a short-range wireless protocol (e.g., Bluetooth Low Energy (BLE) advertisements) broadcast at intervals on the order of 100 milliseconds to 10 seconds are believed to work well.

Automatically sending status messages to the management server any time the AED detects a change in state (and especially a change in a reported state) is a powerful tool for keeping the management server fully up to date on the status of the monitored AEDs, which allows the information presented to telecommunicators, contacts and administrators to be accurate in real time. This can be especially important during emergency use of the AED. Examples of events that trigger the sending of a new status message during emergency use of the AED include any or all of: (i) when the AED is activated for an emergency use; (ii) any time there is a user input to the device (e.g., when the touch-screen pressed, a button pushed, or a setting is changed—for example, when an on/off button is pushed, when a language button is pushed that selects a language for user instructions, when a mode selection button is pushed that selects whether the AED is to be used in an adult or pediatric mode, etc.); (iii) when an electrode pad cartridge is opened or the electrode pads are otherwise accessed; (iv) each time the AED's instruction state changes; (v) when the AED determines that the electrode pads have been placed on a patient (which is often inferred by a detecting an impedance between the electrode pads that is consistent with placement of the pads on a patient); (vi) when the detected impedance changes significantly (which may suggest that the pad are no longer attached well to a patient); (vii) each time that the AED performs a classification of the patient's cardiac rhythm; (viii) when a determination is made that the patient has a shockable heart rhythm; (ix) each time a defibrillation shock is delivered; (x) when the AED determines that a normal (or non-shockable) cardiac rhythm has been restored; (xi) when the AED is turned off (e.g., when the AED is powered off at the end of a use by pressing an on/off button); (xii) when a pad cartridge is reinserted in the AED (or the electrode pads are otherwise placed back in their storage position); (xiii) when CPR is started; (xiv) when CPR is stopped; (xv) when CPR performance measurements change; (xvi) any device state change, etc.

The form and specific content of the status messages may vary widely in accordance with the needs and design goals of any particular embodiment, the capabilities of the AEDs and the context in which the status messages are sent. For example, in many cases, the status messages sent during emergency use of the AED will have at least some different content than status messages sent when the AED is in a standby mode.

In one particular embodiment, the status message includes: a message identifier, an AED serial number, a hardware version identifier, a software version number, an electrode pad serial number, an electrode pad expiration date, a battery charge level, a series of status flags and indicators, a series of functionality flags and indicators, a number of indicators and timestamps associated with reporting emergency use of the AED, and location information.

The message identifier identifies the message as a status message. The serial number field indicates the serial number of the reporting AED. The hardware version identifier indicates the hardware version number of the AED. The software version number indicates the software version number that is currently installed on the AED. In some implementations, the software version number also includes the software build number. The electrode pad serial number provides the serial number of the electrode pad or pad cartridge currently installed on the AED. The electrode pad expiration date provides the expiration date of the installed electrode pads. The battery charge level provides the charge level of the AED's battery. In some embodiments, the AED reports the charge level as a percentage.

The functionality status flags and indicators provide general information about the AED. The specific flags used in any particular implementation may vary widely, but in the illustrated embodiment, the flags include: (i) a BLE authentication flag that indicates whether or not the AED's Bluetooth Low Energy (BLE) functionality has been authenticated; (ii) an emergency mode flag that indicates whether or not the AED has been activated in an emergency mode; (iii) a BLE paired flag that indicates whether the AED is currently paired with an external device using an BLE connection; (iv) an electrode pad accessed flag that indicates whether or not the electrode pads have been accessed or removed from the electrode pad cartridge; (v) a patient detected flag that indicates that the electrodes have been placed on a patient, as previously mentioned the AED can detect the presence of a patient by measuring the impedance between the electrode pads and verifying that the detected impedance; (vi) a language flag or indicator that indicates the language currently selected for providing operating instructions (e.g., if English and Spanish are supported by the AED, a first language flag state may indicates that the current operational language is English and a second language flag state indicates that the current operational state is Spanish-if more than two languages are supported, a multi-bit indicator may be used to facilitate unique identification of each supported language; an adult/pediatric operating mode flag that indicates whether the AED is currently in an adult operating mode or a pediatric operating mode; and a files available to send flag that indicates when the AED has files to send to the management server 20.

The emergency use indicators and timestamps include an activation timestamp that identifies the time that the AED was activated for emergency use. In some embodiments, the combination of the device serial number and the activation timestamp form a unique incident ID for each emergency use.

The electrode pads accessed flag is set when the electrode pads are accessed—e.g., by detecting the opening of a drawer that holds the pads, the opening of a lid of a chamber that holds the pads, by detecting the breaking of a seal of a tray, container or packet that holds the pads, etc. In some embodiments, a pads accessed timestamp is also provided to indicate the time that the pads were accessed.

In some embodiments, if the pads are returned to their storage location without being used or soiled in any way, the pads accessed flag may be returned to the "not accessed" state and a timestamp may be provided to indicate the timing of when the pads were replaced.

As previously mentioned, the AED can detect the presence of a patient by measuring the impedance between the electrode pads and verifying that the detected impedance. When an impedance in the expected patient range is detected, the patient detected flag is set to indicate that the electrodes have been placed on a patient. In other embodiments, other sensors can be used to detect the pad placement. In some embodiments, a pad placement timestamp is also provided to indicate the time that the pads were placed on the patient.

If and when the patient is no longer detected, the patient detected flag may be reset and a timestamp provided to indicate the time when at least one of the pads was disconnected. In the relatively rare situation where the pads are applied, disconnected, and reapplied, the corresponding sequence of status messages informs the management server of the sequence and timing of such events.

A classification indicator provides information about the latest patient cardiac rhythm analysis performed by the AED's classifier. The reported information includes (i) a classification timestamp that indicates the time that the classification analysis was performed. (ii) A shockable rhythm flag indicates the classification result—e.g., whether the detected heart rhythm was deemed a shockable rhythm and therefore a shock was delivered, or a non-shockable rhythm was detected. In embodiments in which the classifier identifies the nature of the detected rhythm such information can be included as well. (iii) A shock intensity indicator indicates the intensity or delivered energy of the delivered shock. In implementations in which both adult and pediatric shocks are contemplated and are intended to be delivered with the same energy levels, this may take the form of a flag that indicates whether an adult or pediatric shock was delivered. In embodiments where a wider variety of shock energy levels are expected, a correspondingly larger set of states can be used to convey the delivered energy, or the energy delivered can simply be reported (e.g., 150 joules).

When a shock has been delivered, a shock delivery timestamp may be included to indicate the time that associated shock was actually delivered. In some embodiments, a time since the last analysis is also provided. This indicates the amount of time that has passed since the latest reported classification analysis was performed. In some embodiments, the classification indicators for one or more preceding classifications are also included.

An instruction state identifier indicates the current instruction state of the AED. That is, it indicates which instruction is currently being generated by the AED, which provides additional visibility regarding the current status of the AED.

The status message also preferably reports the current location of the AED together with location accuracy information such as the Circular Error Probability (CEP), an Estimated Position Error (EPE), an Uncertainty Radius and/or other measures of the perceived accuracy of the location information. When available, a confidence level that indicates the confidence that the user's actual location is within the stated accuracy radius is also provided. In some embodiments, the location information also includes an indicator or flags that indicate the type of position sensing that was used to determine the location—e.g., GPS (or other GNSS system), a cellular positioning system, a Wi-Fi positioning system etc. The location accuracy information gives the management server the ability to understand the relative precision, quality and reliability of the reported AED location.

In some embodiments, the status message also gives the signal strength of wireless connections—e.g., cellular signal strength, Wi-Fi signal strength, satellite signal strength, etc.

Although a specific status message structure has been described, it should be appreciated that the AED may be configured to transmit a number of different status messages at different times and that the contents of any particular status message may vary widely based on the needs of any particular system and system design goal. Therefore, the description of the status message set forth above should be understood to be exemplary in nature, and a number of other message formats can be used to convey pertinent information to the management server. By way of example, a few other representative status messages are described in U.S. Pat. No. 11,077,312 (P016B); U.S. Pat. No. 11,210,020 (P021) and U.S. Pat. No. 11,640,755 (P021X1), which are incorporated herein by reference.

Since status messages are sent frequently to the management server during emergency use, preferably including each time there is any AED state change or user input, the management server has good visibility of the incident in real-time and can thereby provide incident notifications and/or incident reports to interested parties in real-time during emergency use of the AED.

Although the primary described embodiments utilize somewhat standardized periodic status messages to inform the management status of the AEDs during emergency use of the AED, in other embodiments more distinct messages can be sent when various events occur, and the structure of the messages can vary widely based on the nature of the information being conveyed and the communication technology being used to transport the messages.

Incident Notifications

There are many situations where it may be desirable to notify selected entities, individuals and/or endpoints when an AED is used. Since the AED 10 regularly reports its status to the management server 20 any time it is activated, the management server can be configured to send incident notifications to interested parties as desired in real-time during use of the AED. There are a wide variety of different AED use scenarios and the specific entities/individuals/endpoints etc. (collectively referred to as notification targets) that it is desirable to notify may vary significantly based on the context. When an AED is used to treat a potential cardiac arrest incident, it is a medical emergency, so it is often desirable to notify the responsible PSAP to: (1) help ensure that EMS is dispatched to the incident in a timely manner; (2) give the telecommunicator at the PSAP additional insight as to what is happening at the incident location; and (3) help ensure that EMS is heading to the correct precise location. An example of the usefulness of the precise location is a cardiac arrest that occurs at a high school. On the school property, being able to differentiate between the incident being located at the baseball field vs. at the front entrance of the high school can have a significant impact on EMS response time.

For AEDs managed by an entity, in many circumstances it may be desirable to notify one or more administrators or responders associated with the AED of the incident. For example, when the AED is owned by a business, it may be desirable to notify the business owner, or an administrator of the business's AED program. Similarly, when the AED is owned by a governmental agency, it may be desirable to notify the administrator responsible for the AED. For AEDs owned by an individual, it may be desirable to notify the owner, family members, friends and/or neighbors of the incident. For AEDs prescribed for patients that are particularly susceptible to cardiac arrest, it may be desirable to additionally notify prescribing doctor or medical facility. Of course, there are many other examples as well.

Figure 2:
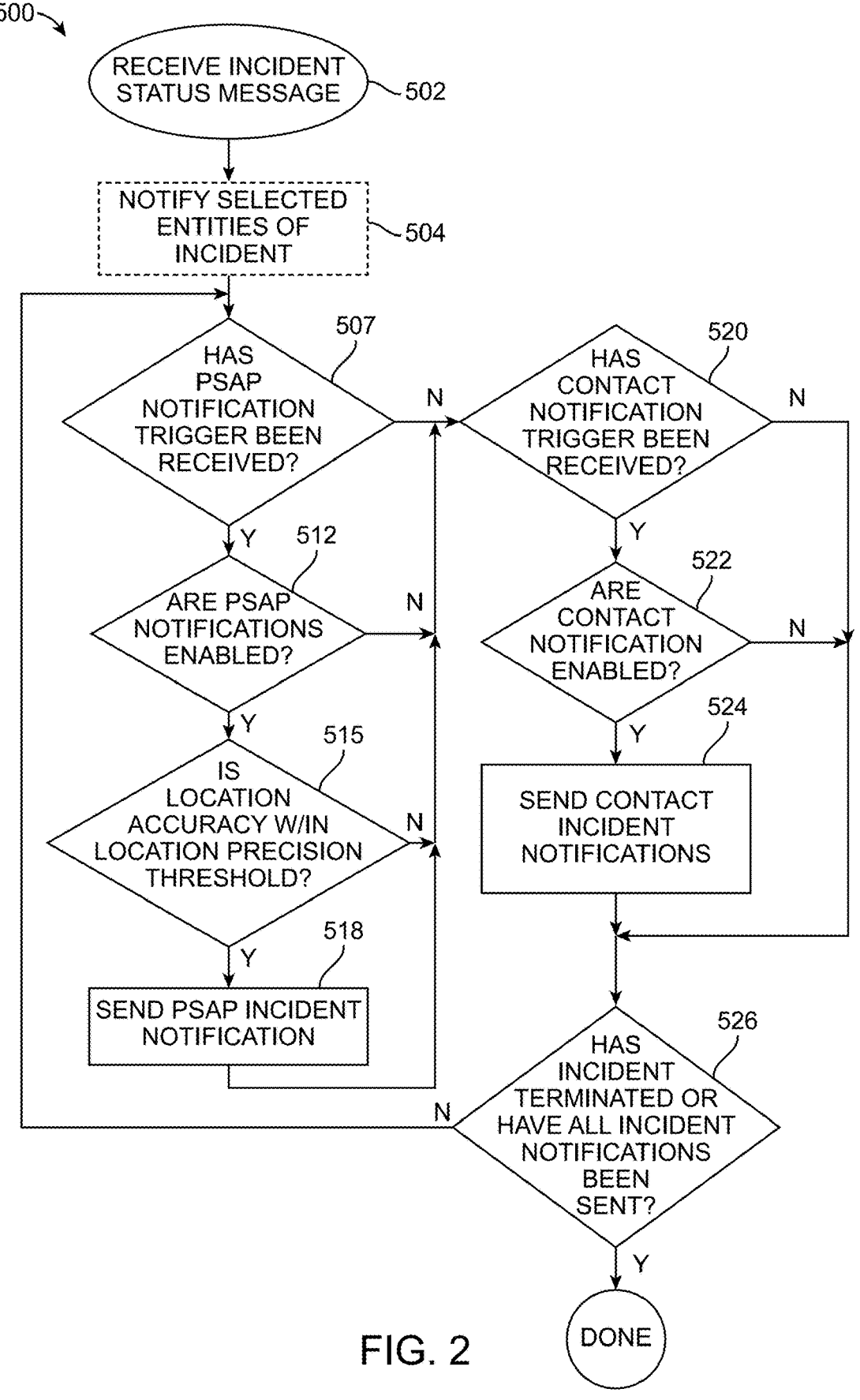
FIG. 2 is a flow chart illustrating a management server-based method for notifying a PSAP and others of the deployment of an AED in accordance with an embodiment.

Referring next to FIG. 2, a management server-based method of conveying incident notifications to PSAPs and others in accordance with one embodiment will be described. As described above, the AEDs 10 are designed to automatically send status messages to the management server 20 in real time during emergency use of the AEDs. The described approach begins with the reception of an incident status message (e.g., the first status message associated with an incident) from an AED that indicates that has been activated. Block 502. In the described embodiment, the AEDs 10 are configured to send an incident status message to the management server 20 as soon as they are activated, and the activation flag (or other suitable mechanism) indicates that the AED has been activated. The incident status message includes an incident ID that is unique to the incident and all status messages sent by the activated AED during the incident include the same incident ID, so it is easy for the server 20 to associate any received status message with the associated incident. There are several things that the management server does when the first incident status message is received including creating an incident record in an incident database (which may be part of the management database 90 or a separate incident database) and making real-time incident reports available (e.g., to interested parties including medical and EMS personnel and parties associated with the activated AED).

In some circumstances, it is desirable to notify certain entities of the incident substantially immediately after the first incident status message is received as represented by block 504. For example, it may be desirable to notify one or more administrators associated with the AED that the AED has been activated if they have opted into such incident notifications. Such administrator notifications can be sent via text messaging, instant messaging, e-mail, fax or any other appropriate medium.

When AED activated based incident notifications are supported, the management server checks the management database 90 to determine whether there are any individuals or entities associated with the activated AED that are to be notified of the incident (notification targets) based on the activation of the AED. If so, incident notifications are sent to the designated individuals/entities.

A drawback to sending incident notification based on the initial activation of the AED is that there is a (non-trivial) risk that the AED was turned on for reasons other than to respond to a potential cardiac arrest. For example, an owner, administrator, employee, bystander may purposefully or accidentally activate the AED (e.g., push the "on/off" button or opening the pad cartridge) as they are interacting with the AED to see how it works or trying to service the AED. Thus, sending incident notifications based on the initial activation of the AED will statistically result in a number of notifications being sent in a variety of non-emergency situations. In some circumstances, sending incident notification in non-emergency settings may be highly undesirable. For example, it is typically highly undesirable to send an incident notification to a PSAP to thereby initiate an emergency response in non-emergency settings. On the other hand, some individuals may wish to be notified anytime the AED is activated. For example, if the AED is located in a school, the school nurse or responsible administrator may wish to be notified any time the AED is activated, even if the activation is for non-emergency purposes.

Preferably notifications 504 that are sent based on activation of the AED are transmitted on an opt-in basis. That is, the recipient has requested to be notified any time that the AED is activated.

To mitigate the risk of sending notifications in non-emergency situations, events other than device activation can be used to trigger the sending of some or all of the incident notifications as represented by block 507. For AEDs, one particularly good trigger is when the electrode pads have been placed on a patient. This is because pad placement typically occurs early in the AED deployment process and rarely occurs in non-emergency settings.

The AED can reliably detect when the pads have been placed by measuring the impedance between the electrode pads. As previously mentioned, when the AED detects that the pads have been placed, a status message reporting the pad placement is sent to the management. When the management server receives a status message indicating that the pads have been placed, it can use that as a trigger for initiating selected notification processes (such as emergency services and/or other entity notification processes) as represented by blocks 507 and 520.

Although pad placement works well as an emergency notification trigger, other events can be used as the notification trigger in other embodiments. One of the next things that the AED typically does after the pads have been placed is to measure and classify the patient's heart rhythm to determine whether the patient has a shockable heart rhythm. The AED 10 reports each classification that it performs, as well the results of such classification (e.g., that the patient has a shockable or non-shockable heart rhythm). Typically, a short ECG segment (e.g., a segment on the order of 3-15 second) is used for such classifications. Therefore, the delay between pad placement and initial rhythm classification is often short enough that rhythm classification may be used as a substitute for pad placement as the emergency notification trigger. A drawback of using rhythm classification as a notification trigger is that it delays the notification relative to pad placement triggered notifications. An advantage is that it potentially further reduces the probability of sending notifications in non-emergency situations.

Alternatively, the notification trigger may be based on the results of the classification. For example, notifications may only be triggered if/when a shockable heart rhythm (or other heart rhythm indicative of an emergency) is detected. Such a trigger still further reduces the probability of sending notifications in non-emergency situations since there is clearly an emergency situation if the victim has a shockable heart rhythm. However, it has the drawback of not sending notifications in a variety of emergency situations where the victim may require medical assistance but is not in cardiac arrest. Since circumstances in which a public access AED is deployed and the electrode pads are placed in non-emergency situations is understood to be quite low, pad placement or "classification performed" triggers are generally preferred to a shockable rhythm detection-based trigger in most implementations.

In still other circumstances, the notification trigger can be based on a user accessing the electrode pads e.g., by opening a pad cartridge or container. An advantage of using pad access as the notification trigger is that it occurs earlier in the process than pad placement. A disadvantage is that it is more likely to prompt notifications in non-emergency situations than a pad placement-based trigger, although it is less likely to prompt non-emergency notifications than a simple activation-based trigger.

In other situations, the notification trigger may be based on a user accessing the electrode pads by opening a sealed chamber or container that holds the electrode pads while the AED is activated. This is distinguished from acts like merely opening an unsealed compartment that holds the pads or pulling a sealed drawer from a cartridge that holds the pads. Triggering based on "breaking a seal" for the pad reduces the risk of non-emergency notification since users that are "playing" with the AED or maintain the AED are far less likely to break a pad seal than merely open an unsealed chamber to see where the pads are located. Although seal breaking works well as a trigger, a drawback is that many AEDs are not configured to detect seal breaking.

When an incident trigger is received, the server 20 checks to determine whether PSAP notifications are enabled (block 512) and whether contact notifications are enabled (block 522).

PSAP Notifications

When a Public Safety Answering Point (PSAP) is notified of an incident, one of the pieces of information that they require is the location of an incident so that EMS personnel can be dispatched to the proper location. Since the AED 20 includes its current location in the status messages, that current location information is reported to the PSAP as part of the PSAP notification. A problem that sometimes occurs when using device reported locations is that the reported locations may not be accurate. For example, in the context of a dense city, if the incident location is only known within a region of several blocks, there is a significant risk that an EMS unit dispatched to the reported location would be unable to find the incident in a timely manner. It is wasteful of EMS resources to dispatch an EMS unit to the wrong location and any system that would repeatedly trigger EMS dispatch to wrong locations is unlikely to be adopted or continued.

Most positioning systems (e.g., GPS, Cellular Network Positioning, Wi-Fi Positioning (WPS), BLE Positioning, etc.) report both the determined location and some type of accuracy measure and/or location accuracy confidence value. For example, GPS systems (and other GNSS systems) typically output an estimated position error (EPS) that indicates the perceived accuracy of the reported location. Cellular and Wi-Fi positioning systems often indicate an uncertainty radius that provides an estimated radius within which the actual position is likely to be located often together with a confidence level that provides a percentage indicating the confidence that the device's location actually falls within the specified radius. For the purposes of this application, these types of information, and similar information provided by other positioning systems are collectively referred to as location accuracy measures.

Referring again to FIG. 2, the management server checks the management database 90 to see whether PSAP notifications are enabled for the activated AED. When PSAP notifications are enabled (the yes branch from block 512), the management server determines whether the AED's location is accurately known. As previously mentioned, the status messages sent by the AED include both the AED's location and one or more location accuracy measures indicative of the perceived accuracy of the location measurement. The location accuracy measure(s) are used by the server to determine whether the location of the AED is known precisely enough to justify notifying the PSAP of the incident. This can be done by checking to see if the location accuracy reported by the AED is within a predetermined location precision threshold. Block 515. If so, the management server sends an electronic incident notification message (referred to herein as a PSAP notification message) that causes an emergency services call center responsible for handling medical incidents in a region that includes the location of the AED to be notified of the emergency use of the AED. Block 518.

Different PSAPs may have different thresholds for how accurate they want the location information to be before they are notified of an incident and, if desired, the specific location precision threshold used by the server can be dependent on the target PSAP. That is, different location precision thresholds may be used for different target PSAPs. In some embodiments, a default location precision threshold is used for most PSAPs, but the default for any geographic region can be adjusted based on the preferences of/requests from the responsible PSAPs. In other implementations different default precisions may be used for different PSAPs (e.g., based on jurisdiction or the nature of the region served), or different defaults may be used for different regions covered by a single PSAP as desired. In still other implementations, a single default precision may be used for all PSAPs.

In the embodiment described above, the management server 20 makes the determination of whether the location of the incident is known well enough to justify contacting emergency services based on the location accuracy measurements. However, in other embodiments, that decision can be made by other nodes in the response chain.

The PSAP notification message may take a variety of forms. Preferably, it includes the incident ID and both the location of the incident and the reported location accuracy measure(s). It may also include other information such as the current state/instruction state of the AED. In some embodiments, the server 20 looks up the responsible PSAP based on the geographic location of the incident and sends the PSAP notification message directly to the responsible PSAP. In other embodiments, the PSAP notification message is sent to an Emergency Services Interface 28 which identifies the responsible PSAP and sends an appropriate electronic incident notification to the responsible PSAP. As described above, using an ESI 28 such as RapidSOS or other similar services as an intermediary can be advantageous because they are already integrated with a large number of PSAPs.

Some (indeed many) PSAPs do not currently have processes set up for integrating electronic incident notifications into their response workflows. For incidents that occur at locations within the jurisdiction of such PSAPs, the PSAP notifications can be sent to a call center 29 that initiates a voice call to the responsible PSAP and verbally informs the dispatcher of the incident, its location and any other relevant incident information. In some embodiments, the ESI also includes a call center 29 so the ESI takes responsibility for both electronic notifications (when electronic notifications are supported by the target PSAP) and voice calls (when electronic notifications are not supported).

Contact Notifications

In parallel with the PSAP notifications, the server 20 may notify any other entities, persons or endpoints of the incident that the specified in a contact list by an administrator. Thus, the server determines whether a contact notification trigger has been received as represented by block 520 and whether contact notifications have been enabled as represented by block 522. If a contact trigger has been received and contact notifications are enabled, then incident notifications are sent to the identified contacts as represented by block 524.

It should be appreciated that the event(s) that trigger contact notifications may be the same as, or different than the event(s) that trigger PSAP notifications. In FIG. 2, separate checks are shown for determining whether a PSAP notification trigger (block 507) and a contact notification trigger (block 520) have been received for in order to help emphasize that in some embodiments, different triggers may be used for these two types of notifications. For example, PSAP notifications may be triggered based on detected pad placement and location accuracy measures, whereas contact notifications may be based on activation of the AED, the user accessing the electrode pads or some other event trigger. However, in many implementations, a single notification trigger is used and/or these checks may be accomplished in a single step.

In the flow chart of FIG. 2, the contact notification process is shown as following the PSAP notification process for easy of description. However, as will be appreciated by those skilled in the art, these processes may readily be performed in parallel, in reverse order, or in a staggered manner.

In the illustrated embodiment, the location accuracy test is required for PSAP notifications but is not required for contact notifications. In other embodiments, the location accuracy test may also be required for contact notifications. In still other embodiments, some contact notifications may require the location accuracy test, while others do not. When location accuracy tests are required for contact notifications, the required location accuracy may be the same, or different than the location accuracy required for PSAP notifications.

There are a wide variety of different AED use cases and different scenarios may warrant different categories of individual being notified of an incident. In some cases, the appropriate trigger events that result in incident alerts being sent to different contacts may vary. For example, in the setting of a fitness center chain or retail store chain having a large number of different locations, both a local manager and a corporate administrator may desire to be notified when an AED that they are responsible for is used. However, their preferences with respect to when to receive notifications may differ. For example, the local manager may wish to be notified any time that the AED is activated so they can immediately respond, whereas the corporate administrator may only wish to be notified when the AED is used on a patient (e.g., when the pads are placed or even when the incident is completed). Similarly, when an AED is prescribed for a patient that is particularly susceptible to cardiac arrest, both family members and the prescribing doctor may wish to be notified when the AED is used. The family members may wish to be notified anytime the AED is activated, whereas the doctor may only wish to be notified if/when the AED is actually used on the patient so that they have substantially immediate access to the incident report which may include the ECG of the patient detected during use of the AED. Of course, there are many other notification use scenarios.

To facilitate customization of the notifications, a management platform user interface may be provided that allows the AED's administrator(s) to set notification preferences for any particular AED, or any group of AEDs associated with the administrator.

U.S. patent application Ser. No. 18/653,267 (P027A) and Ser. No. 18/653,274 (P027B), which are incorporated herein by reference, describe a management platform user interface that enables administrators to set various preferences and settings associated with one or more AEDs that they are responsible for. Such a platform can also be used or adapted to allow the administrator to set incident notification preferences as described herein.

Figure 3:
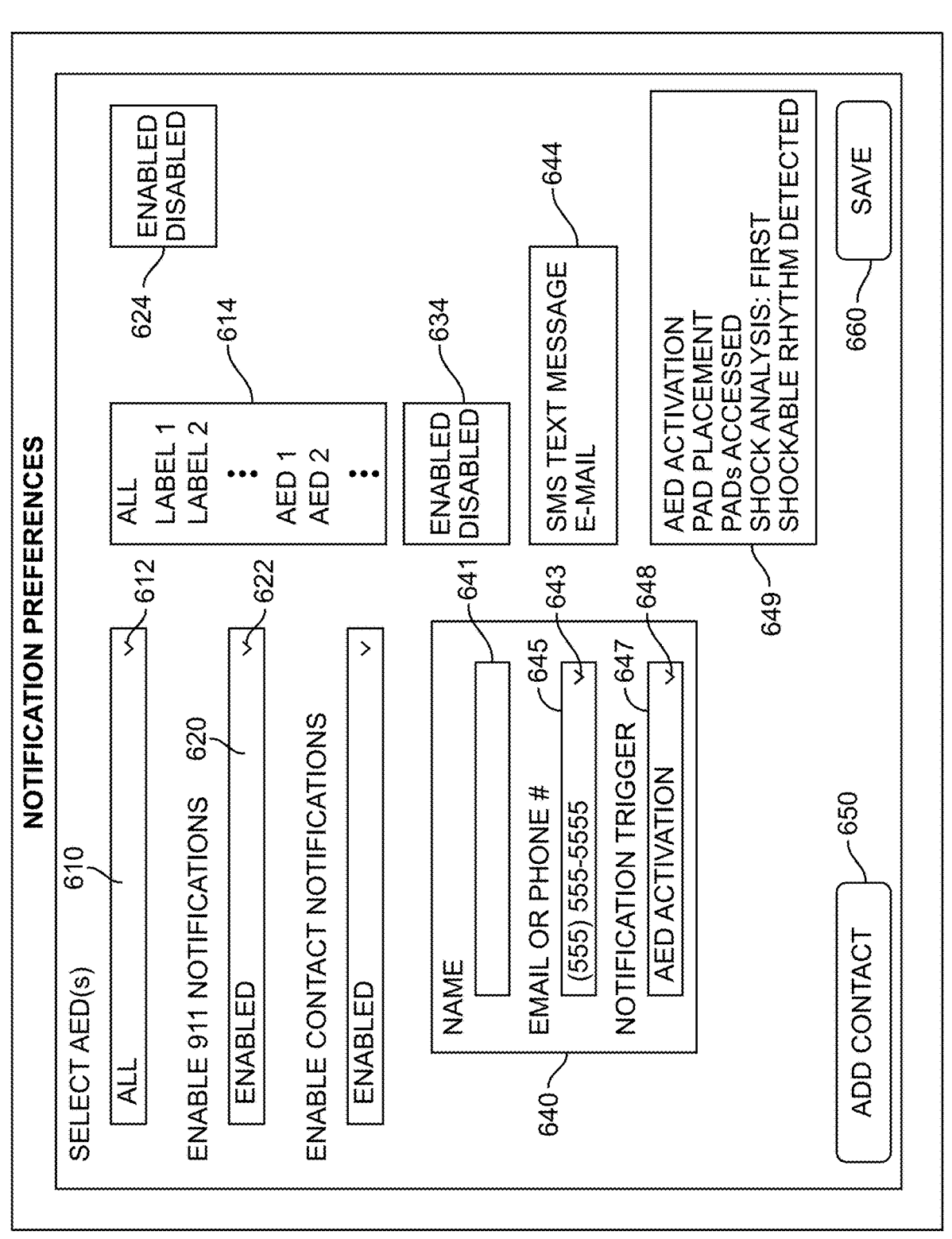
FIG. 3 is a screenshot of notifications settings page of a computer-based AED management platform user interface in accordance with an embodiment.

Referring next to FIG. 3, an AED management platform user interface that facilitates administrator selection of desired AED notification preferences in accordance with an embodiment will be described. The illustrated notification preference page 600 includes an AED selector 610, a PSAP notifications selector 620, and a contact notification selector 630. The AED selector 610 allows the administrator to select the AED(s) or groups of AEDs that they wish to apply the selected settings to. In some embodiments, the AED selector 610 includes a menu activator 612, that when activated causes a menu 614 to be rendered (e.g., a pull-down menu, a chooser dialog box, etc.) that enables the administrator to choose the desired AEDs. In the illustrated embodiment, the menu 614 include an "All" category, one or more group labels, and one or more individual AEDs. When the "All" entry is selected, the designated settings are applied to all AEDs associated with the administrator. When a group label is selected, the designated settings are applied to all AEDs in the identified group. Group labels are described in more detail in the incorporated U.S. patent application Ser. No. 18/653,267 (P027A) and Ser. No. 18/653,274 (P027B). When an individual AED is selected, the designated settings are applied to the selected AED(s). In some embodiments, the administrator may select multiple labels and/or AEDs in parallel, such that the designated settings are applied to all of AEDs in multiple groups and/or to multiple designated AEDs in parallel.

The PSAP notifications selector 620 allows the administrator to enable or disable PSAP notifications. The notification selector 620 includes a menu activator 622, that when activated causes a menu 624 to be rendered. In the illustrated embodiment, the menu 624 includes "enable" and "disable" (or "off") entries. When enable is selected, PSAP notifications will be sent (if appropriate) when the AED is used. When disable is selected, PSAP notifications will not be sent.

The contact notification selector 630 also has a menu activator 632, that when activated causes a menu 634 to be rendered. In the illustrated embodiment, the menu 634 includes "enable" and "disable" (or "off") entries. When enable is selected, contact notifications will be sent to identified contacts when the AED is used. When disable is selected, contact notifications will not be sent.

When contact notifications are enabled, a contact dialog box 640 appears that allows the administrator to enter the name and contact information of the person(s) or entity(ies) to be contacted. The contact dialog box 640 may include a name field 641, a notification type selector 643, and a contact address/phone number field 645. The administrator then enters the contact's name in field 641, and selects the type of notification desired (e.g., via SMS text messaging, e-mail, or other pathway) using notification type selector 643 and the appropriate destination address (e.g., e-mail address, phone number, etc.) in contract address/phone number field 645. When desired, the administrator may select multiple notification paths (e.g., both text and e-mail). In the illustrated embodiment, selection of notification type selector 643 causes a notification type menu 644 to be rendered from which the administrator can choose the desired notification pathway. In the illustrated embodiment, e-mail and text messages are supported, but in other embodiments, other suitable notification pathways including other messaging technologies, faxing, etc.

In some embodiments, the dialog box 640 also includes a notification trigger selector 648 that allows the administrator to select what event they want to trigger the notification to the designated contact. For example, in the illustrated embodiment, the notification trigger selector 647 includes a menu activator 648, that when activated causes a menu 649 to be rendered (e.g., a pull-down menu, a chooser dialog box, etc.) that enables the administrator to choose the desired notification trigger. In the illustrated embodiment, the menu 649 lets the administrator choose between AED activation, pads accessed, pad placement, shock analysis performed, and shockable rhythm detected. Of course, in other embodiments, fewer, different and/or more triggers can be listed.

The notification preference page also includes an Add contact GUI widget 650 that when activated instantiates another contact dialog box 640 that allows the administrator to designate another person or entity to be notified of the incident and provide their contact information and notification preferences. A "Save" GUI widget 660 is also provided. When the Save GUI widget is selected, the management platform sends a notification preferences update message to management server 10 that indicates the entered notification preferences. The management server then updates the management database 90 accordingly thereby applying the desired preferences to the target AEDs.

In the embodiment illustrated in FIG. 3, the administrator is given great flexibility in that different notification triggers can be used for different individual contacts. However, in other embodiments, a single contact notification trigger selected by the administrator is applied to all contacts or the contact notification trigger may be defined by the system designer such that the administrator is not given control over what specific events trigger content notifications. As previously mentioned, the contact notification trigger(s) may be the same or different than the PSAP notification trigger.

There are some (relatively unique) circumstances where an owner of an AED may want to configure their AEDs to contact a particular PSAP if/when the AED is used as opposed to having the system independently determine which PSAP to notify of the AED's use. If it is desired to broadly provide the ability for administers to identify the desired target PSAP, a PSAP selector (not shown) may be added to the notification preference page 600 of the management platform user interface. Alternatively, the PSAP selector may be provided at other locations within the user interface—or simply be associated with AEDs associated with a particular owner.

An example use case for using a target PSAP is the context of a large theme park, which may have its own emergency dispatch service (which is considered a PSAP for the purposes of this application) for incidents that occur within the boundaries of the theme park. Such owners, which may have a fleet of hundreds of AEDs within the theme park, may prefer to have their own, quasi private PSAP notified of incidents occurring within the park rather than the PSAP that is responsible for the area around the park. As with other preferences, any target PSAP selection may be applied to individual AEDs, to a group or groups of AEDs (e.g., all AEDs associated with a particular label), to all AEDs associated with a particular entity, or at any other desired level.

FIG. 3 illustrates one way providing administrator control of enabling PSAP notifications for their devices. In other embodiments, a GUI widget such as an "enable QuickRescue" or "enable 911 Notifications" button or other selection mechanism on an organization Settings page in a management platform user interface can be provided to allow the administrator to opt-in to PSAP notifications for all of the devices associated with the administrator. Additionally, or alternatively, an AED status page, or an edit AED record page in the management platform user interface can have a GUI widget that allows the administrator to globally enable or disable PSAP notifications for all of their associated devices. Such pages and editing mechanism are described in U.S. patent application Ser. No. 18/653,267 (P027A) and Ser. No. 18/653,274 (P027B) which are incorporated herein by reference.

The described incident notification approach can be used in conjunction with any AED that is capable of communicating its status and/or relevant messages to a remotely located server during emergency use of the AED. By way of example, and not by limitation, a representative defibrillator system 100 will be described. The illustrated defibrillator utilizes a modular architecture that is well suited for use in automated external defibrillators (including both semi-automated and fully automated defibrillators) although it may also be used in manual defibrillators and hybrid defibrillators that may be used in either automated or manual modes.

Figure 4:
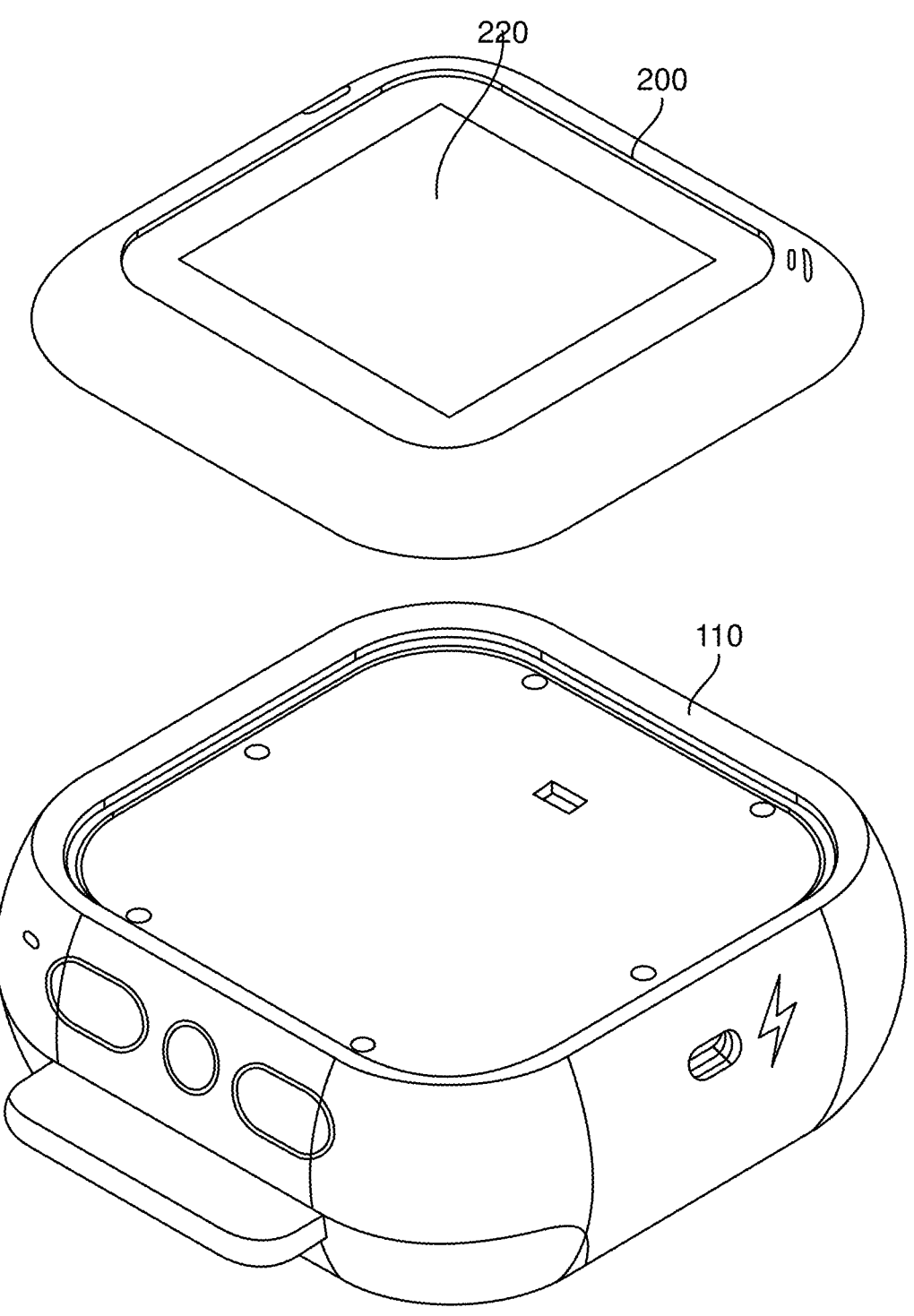
FIG. 4 is a diagrammatic representation of a modular defibrillator system architecture.

The core of the modular defibrillator system 100 is a base defibrillation unit (base unit) 110 as seen in FIG. 4. The illustrated base defibrillation unit 110 is a fully functional AED that is configured such that its functionality can be supplemented by attaching an interface unit 200 to the base unit. The base unit 110 independently functions as an AED both with and without the attached interface unit 200. In this embodiment, interface unit 200 includes one or more processors, a touch sensitive display screen 220, a communications unit and preferably its own power storage unit (e.g., battery). The touch sensitive display facilitates user interactions with the interface unit and, as appropriate, indirect interactions with the base unit. The communications unit facilitates communications with external systems and/or devices using a variety of different communications technologies and protocols, as for example, Wi-Fi communications, cellular communications, satellite communication and short-range wireless communications technologies (e.g., Bluetooth, Near Field Communication (NFC), etc.) By way of example, U.S. Pat. No. 10,773,091 (P006E), U.S. Pat. No. 10,737,105 (P006A), U.S. Pat. No. 11,452,881 (P016A), U.S. Pat. No. 11,077,312 (P016B) and U.S. patent application Ser. No. 17/007,838 (P019B), each of which is incorporated herein by reference, describe details of a variety of such modular defibrillator architectures.

Figure 5:
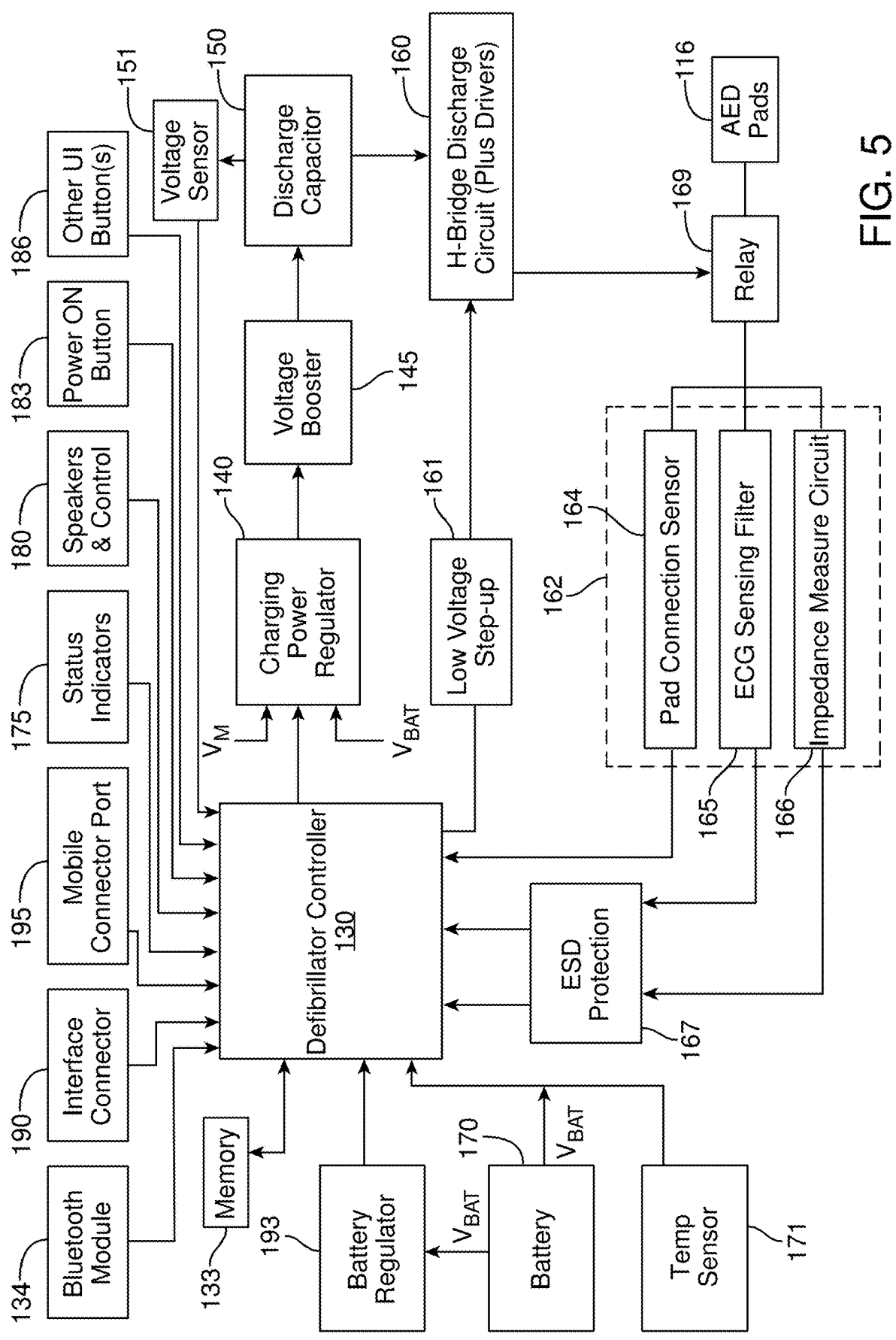
FIG. 5 is a block diagram illustrating electrical components of a representative defibrillator unit.

FIG. 5 is a block diagram illustrating one representative electronics control architecture and associated components suitable for use in the base defibrillator unit 110. In the illustrated embodiment, the electronic components include a defibrillator controller 130, memory 133, a wireless communications module in the form of Bluetooth module 134, a charging power regulator 140, a voltage booster 145 (which may have multiple stages), a high voltage capacitor 150 for temporarily storing sufficient electrical energy suitable to provide a defibrillation shock, discharge control circuitry 1160, pad related sensing circuitry 162 and relays 169, power storage unit 170, battery regulator 193, status indicator(s) 175, speaker(s) 180 and one or more electrical connectors (e.g., interface connector 190, mobile connector port 195, charger connector (not shown), etc.). The charging power regulator 140 and voltage booster 145 which cooperate to control the charging of the shock discharge capacitor 150 are sometimes referred to herein as a charging circuit.

The defibrillator controller 130 is configured to control the operation of the base defibrillator unit and to direct communications with external devices, as appropriate. In some embodiments, the defibrillator controller includes one or more processors arranged to execute software (some or all of which may take the form of firmware) having programmed instructions for controlling the operation of the base unit, directing interactions with a user and communications with external components. The software may be installed on the memory 133. Although the singular term memory is often used herein, it should be appreciated that the memory may be divided into multiple different parts which take any suitable form or combination of forms (e.g., various types of RAM, ROM, PROM, EEPROM, etc.) Unless the context suggests otherwise, references to "memory" herein are intended to cover all suitable forms and combinations of physical memory. Similarly, although the singular term "processor" is often used herein, it should be appreciated that any appropriate number of processors and/or processing cores can be utilized and unless the context suggests otherwise, references to "processor" herein are intended to cover processing units composed of one or more physical processors or processing cores.

The base defibrillator unit 110 may optionally be configured so that it is capable of drawing power from certain other available power sources beyond power storage unit 170 to expedite the charging of shock discharge capacitor 150. The charging power regulator 140 is configured to manage the current draws that supply the voltage booster, regardless of where that power may originate from. For example, in some embodiments, supplemental power may be supplied from a mobile device coupled to mobile connector port 195 or from a portable charger/supplemental battery pack coupled to charger connector 197.

The voltage booster 145 is arranged to boost the voltage from the operational voltage of power storage unit 170 to the desired operational voltage of the discharge capacitor 150, which in the described embodiment may be on the order of approximately 1400V-2000V (although the defibrillator may be designed to attain any desired voltage). In some embodiments, the boost is accomplished in a single stage, whereas in other embodiments, a multistage boost converter is used. A few representative boost converters are described in the incorporated U.S. Pat. No. 10,029,109. By way of example, in some embodiments, a flyback converter, as for example, a valley switching flyback converter may be used as the voltage booster 145—although it should be appreciated that in other embodiments, a wide variety of other types of voltage boosters can be used.

A voltage sensor 151 is provided to read the voltage of the capacitor 150. The voltage sensor 151 may take the form of a voltage divider or any other suitable form. This capacitor voltage reading is utilized to determine when the shock discharge capacitor 150 is charged suitably for use. The sensed voltage is provided to controller 130 which determines when the capacitor 150 is charged sufficiently to deliver a defibrillation shock. The capacitor 150 can be charged to any desired level. This can be useful because different defibrillation protocols advise different voltage and/or energy level shocks for different conditions. Furthermore, if the initial shock is not sufficient to restart a normal cardiac rhythm, some recommended treatment protocols call for the use of progressively higher energy impulses in subsequently administered shocks (up to a point).

The discharge circuitry 160 may take a wide variety of different forms. In some embodiments, the discharge circuitry 160 includes an H-bridge along with the drivers that drive the H-bridge switches. The drivers are directed by defibrillator controller 130. The H-bridge outputs a biphasic (or other multi-phasic) shock to patient electrode pads 116 through relays 169. The relays 169 are configured to switch between an ECG detection mode in which the patient electrode pads 116 are coupled to the pad related sensing circuitry 162, and a shock delivery mode in which the patient electrode pads 116 are connected to H-Bridge to facilitate delivery of a defibrillation shock to the patient. Although specific components are described, it should be appreciated that their respective functionalities may be provided by a variety of other circuits.

The pad related sensing circuitry 162 may include a variety of different functions. By way of example, this may optionally include a pad connection sensor 164, ECG sensing/filtering circuitry 165 and impedance measurement chip/block 166. The pad connection sensor is arranged to detect the pads are actually connected to (plugged into) the base defibrillator unit 110. The ECG sensing/filtering circuitry 165 senses electrical activity of the patient's heart when the pads are attached to a patient. The filtered signal is then passed to defibrillator controller 130 for analysis to determine whether the detected cardiac rhythm indicates a condition that is a candidate to be treated by the administration of an electrical shock (i.e., whether the rhythm is a shockable rhythm) and the nature of the recommended shock. When a shockable rhythm is detected, the controller 130 directs the user appropriately and controls the shock delivery by directing the H-bridge drivers appropriately.

In some embodiments, the power storage unit 170 takes the form of one or more batteries such as rechargeable Lithium based batteries including Lithium-ion and other Lithium based chemistries, although other power storage devices such as one or more supercapacitors, ultracapacitors, etc. and/or other battery chemistries and/or combinations thereof may be used as deemed appropriate for any particular application. The power storage unit 170 is preferably rechargeable and may be recharged via any of a variety of charging mechanisms. In some embodiments, the power storage unit 170 takes the form of a rechargeable battery. For convenience and simplicity, in much of the description below, we refer to the power storage unit 170 as a rechargeable battery. However, it should be appreciated that other types of power storage devices can readily be substituted for the battery. Also, the singular term "battery" is often used, and it should be appreciated that the battery may be a unit composed of a single battery or a plurality of individual batteries and/or may comprise one or more other power storage components and/or combinations of different power storage units.

In some embodiments, the base defibrillator unit 110 is capable of drawing power from other available power sources for the purpose of one or both of (a) expediting the charging of shock discharge capacitor 150 and (b) recharging the power storage unit 170. In some embodiments, the battery can be recharged using one or more of the externally accessible connector ports 195, a dedicated charging station, a supplemental battery pack (portable charger), an interface unit 200, etc. as will be described in more detail below. When wireless charging is supported, the base defibrillator unit may include a wireless charging module 174 configured to facilitate inductive charging of the power storage unit 170 (e.g., using an inductive charging station 294, or other devices that support inductive charging, as for example an inductively charging battery pack, a cell phone with inductive charging capabilities, etc.).

The base unit also includes a number of software or firmware control algorithms installed in memory 133 and executable on the defibrillator controller. The control algorithms have programmed instructions suitable for controlling operation of the base unit and for coordinating the described broadcasts, as well as any point-to-point communications between the base unit 110 and the interface unit 200, connected devices, and/or any other attached or connected (wirelessly or wired) devices. These control routines include (but are not limited to): communication control algorithms, heart rhythm classification algorithms suitable for identifying shockable rhythms; capacitor charge management algorithms for managing the charging of the discharge capacitor; capacitor discharge management algorithms for managing the delivery of a shock as necessary; user interface management algorithms for managing the user instructions given by the defibrillator and/or any connected user interface devices (e.g. interface unit 200, mobile communication device 105) during an emergency; battery charge control algorithms for managing the charging of power storage unit 170; testing and reporting algorithms for managing and reporting self-testing of the base unit; software update control algorithms and verification files that facilitate software updates and the verification of the same.

In many installations, an AED will be expected to be stored for long periods of time without being plugged into power and therefore relying solely on battery power. Accordingly, it is important to minimize the power drain as much as possible during this time. In some embodiments, the defibrillator controller is configured to shut down power to all electrical components (including itself) except for (a) a real time clock (not shown), (b) the Bluetooth module 134, and (c) a power controller (not shown) when the AED is in the standby (resting) mode. In some embodiments, the clock and/or the power controller are integrated into the Bluetooth module 134 or an I/O adaptor board that includes the Bluetooth module. The clock is configured to periodically send a status check alarm to the power controller which wakes the power controller up from a sleep mode when the power controller is separate from the Bluetooth module. In response to the status check alarm, the power controller restores power to the entire system. Once power is restored, the defibrillator controller 130 performs a status check and instructs the Bluetooth module 134 to update the standby status message 150 as appropriate. After the status check is performed, the defibrillator controller will again shut down power to all electrical components except the clock, the Bluetooth module 134 and the power controller. The status check alarms can be generated at any desired intervals, as for example, once each day.

With the described power management scheme, the Bluetooth module 134 can continue to broadcast standby status messages even when the AED is powered down.

If the Bluetooth Module 134 makes a connection while the AED is in the standby mode, it sends a message to the power controller, which in turn, powers on the system, thereby allowing the defibrillator controller or other suitable component to communicate with the connecting device. Thus, the AED can effectively be woken up via a Bluetooth connection request. Of course, the power controller is also configured to power the system when a user presses the AED's "ON" button or otherwise activates the AED.

In other embodiments, one or more of the electrical components of the AED, such as the defibrillator controller 130, can be placed in a "sleep" mode rather than being turned off when the AED is in the standby mode. However, a significant advantage of actually turning the defibrillator controller and the bulk of the AED's electrical components off as opposed to placing them in a sleep mode is that it eliminates the power draw associated with the sleep mode, thereby potentially extending the AED's shelf life. It should be appreciated that the power controller/power down approach can be also used with AEDs that don't incorporate a Bluetooth module and/or support the low energy broadcasts described herein.

In some embodiments, a temperature sensor 171 is provided within the defibrillator itself for detecting the internal temperatures of the AED (as opposed to an environmental temperature), which is then used in the temperatures used to trigger the temperature fault notification and clearance messages. Preferable the temperature sensor is positioned adjacent one of the more temperature sensitive components such as battery 170 so that the reported temperature is directly related to the internal temperature of the AED near the temperature sensitive component.

Figure 6:
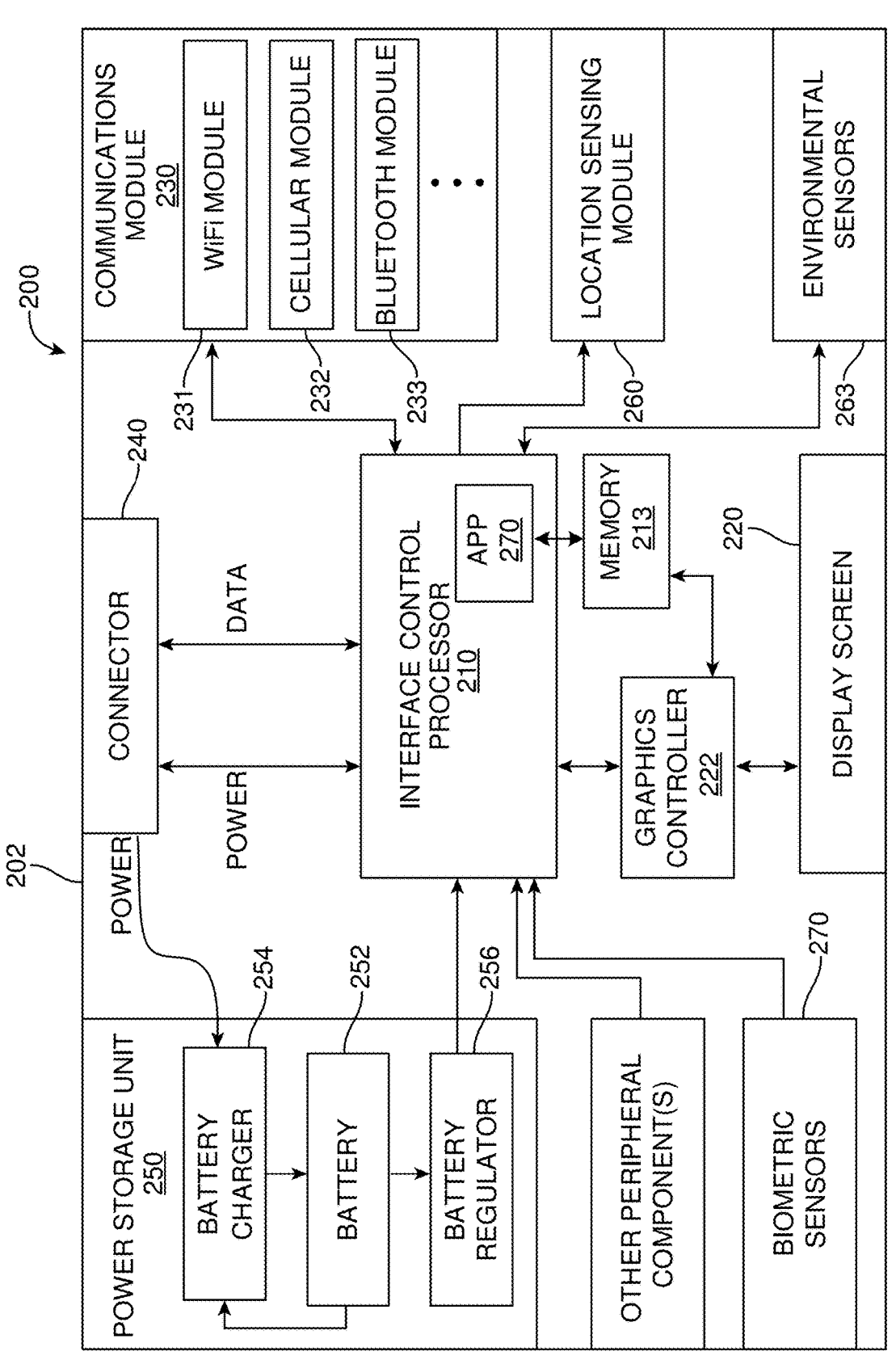
FIG. 6 is a block diagram illustrating electrical components of a representative interface unit.

FIG. 6 illustrates some of the electrical components of a representative interface unit 200. In the illustrated embodiment, the interface unit 200 includes an interface controller (processor) 210, memory 213, a display screen 220, a communications module 230, an electrical connector 240, an interface unit power storage unit 250, and a location sensing module 260, all of which may be housed within the interface unit housing 202. The interface unit has software (which may take the form of firmware and/or an app 270) installed or installable in memory 213 to provide programmed instructions suitable for controlling operation of the interface unit and for coordinating communications between the interface unit 200 and the base defibrillation unit 110 and/or remote devices to provide the described functionalities of the interface unit.

The processor 210 controls operation of the interface unit and coordinates communications with both the base unit 110 and remote devices such as a central server (as will be described in more detail below). In some embodiments, the processor 210 is arranged to execute a defibrillator app 270 or other software that can be used both during use of the defibrillator system 100 during a cardiac arrest incident and to facilitate non-emergency monitoring or/and use of the defibrillator system 100. Similar to the base unit processor 130 discussed above, unless the context suggests otherwise, the processor 210 may take the form of a single processor, multiple processors, multiple processing cores and other processing unit configurations.

The display screen 220 is a touch sensitive screen suitable for displaying text, graphics and/or video under the direction of the processor 210 to assist both during both emergency situations and at other times. The touch sensitive screen is configured to receive inputs based on a graphical user interface displayed thereon. In some embodiments an optional graphics controller 222 may be provided to facilitate communications between the interface control processor 210 and the display screen 220. In other embodiments, functionalities of the graphics controller may be part of the processor 210.

The communication module 230 is provided to facilitate communications with remotely located devices such as the central server. The communications module 230 may be configured to utilize any suitable communications technology or combination of communication technologies including one or more of cellular communications, Wi-Fi, satellite communications, Bluetooth, NFC (Near Field Communications), Zigbee communications, DSRC (Dedicated Short-Range Communications) or any other now existing or later developed communications channels using any suitable communication protocol. By way of example, in the illustrated embodiment, the communications module 230 includes Wi-Fi, cellular and Bluetooth modules 231, 232 and 232 that facilitate Wi-Fi, cellular and Bluetooth communications respectively.

The electrical connector 240 is configured to mate with interface connector 190 on the base defibrillator unit 110. The connectors 190 and 240 are configured to facilitate communications between the defibrillator controller 130 and the interface unit's processor 210. The connectors 190 and 240 are also preferably arranged to supply power from the interface unit 200 to the base unit 110 as will be described in more detail below. In some embodiments, power will only be provided in one direction—i.e., from the interface unit 200 to the base unit 110 and not in the reverse direction during operation. A good reason for this approach is that the defibrillator is the most important component from a safety standpoint, and it is often undesirable to draw power from the base unit to power other devices (including the interface unit 200) in a manner that could reduce the energy available to charge the discharge capacitor in the event of an emergency. However, in some embodiments, the power supply may be bi-directional (at least in some circumstance) if desired—as for example if the base unit is not in use, is fully charged and plugged into an external charging power supply, etc.; or if the power passed to the interface unit is not coming from the base unit's internal battery (e.g., it is coming from a charger, a mobile communication device, or other device connected or attached to the base unit), etc.

The connectors 190 and 240 can take a variety of forms. They can be connectors with accompanying transceivers configured to handle processor level communications (such as UART, SPI, or I2C transceivers), with additional pins for power delivery (Power+GND), and connection verification (i.e. a pin that detects when there is a connection between the interface unit and the Base AED and triggers an interrupt on the Base AED signifying that there is not a unit connected). They can also be more standardized connectors such as USB connectors.

The interface power storage unit 250 provides power to operate the interface unit 210. In many embodiments, the power storage unit takes the form of a battery 252 with associated control components, although again a variety of other power storage technologies such as supercapacitors, ultracapacitors, etc. may be used in other embodiments. The associated control components may include components such as a battery charger and maintainer 254, which may include various safety monitors, and battery regulator 256. Preferably, the power storage unit 250 is rechargeable, although that is not a requirement. In some embodiments it may be desirable to utilize replaceable batteries (rechargeable or not) so that the batteries in the power storage unit 250 can be replaced when they near the end of their useful life. In some embodiments, the power storage unit 250 may also be arranged to supply supplemental power to the base unit 110. Depending on the structure and/or state of the base unit, the supplemental power can be used to help charge the discharge capacitor 150 during use; to power or provide supplemental power for the defibrillator electronics and/or to charge the base defibrillator unit's power storage unit 1170. In other embodiments, a supplemental battery within the interface unit (not shown) may be used to provide the supplemental power for the base unit rather than the power storage unit 250.

The location sensing module may incorporate a variety of technologies including Global Navigation Satellite Systems (GNSS) (e.g., GPS), Wi-Fi positioning, cellular triangulation, assisted GPS, Bluetooth Beacons, Near-Field Communications (NFC) and/or other location determining technologies. When requested, the interface unit can report its current location based on the location sensing technology that is believed to have the best accuracy under the then-present circumstances.

The interface unit may also optionally include various environmental sensors 263 and other peripheral components 266. When desired, the interface unit may include any of a wide variety of different types of sensors and peripheral components. For example, in selected embodiments, the interface unit may include one or more accelerometers and/or gyroscopes, a temperature sensor, a humidity sensor, a time of day or any other desired sensors or components.

The interface unit 200 is preferably configured to securely mechanically attach to the base unit 110. Typically, the interface unit is detachable such that it may be separated from the base unit if desired—although in other embodiments, the attachment may be more permanent in nature. The specific mechanical attachment utilized may vary widely in accordance with the needs of any particular embodiment. In some embodiments, press or form fitting attachment structures are used, while in others, latch and catch mechanisms, snap fit structures, etc. are utilized alone or in combination to releasably attach the interface unit to the base. However, it should be appreciated that a wide variety of other structures can be used in other embodiments. In some embodiments, the interface unit includes an attachment sensor (not shown) that senses when the interface unit is attached to a base unit.

In some embodiments, the interface unit may also include one or more biometric sensors 270. The biometric sensors may vary based on the needs of any particular defibrillator. Some of the biometric sensors may be suitable for use in detecting or evaluating CPR performed during emergency use of the defibrillator. Other biometrics may be useful in more general health management applications. For example, in some embodiments, the biometric sensors may include one or more of a pulse or heart rhythm sensor, a blood pressure sensor, a glucose monitor, a pulse oximeter, an ECG monitor, a sleep tracker, a thermometers, etc.

A benefit of the described modular defibrillator architecture is that the interface unit can be (and preferably is) designed to provide robust connectivity, effectively making the defibrillator a highly connected device. The relatively large touch sensitive display screen provides an interface that can be easily used by users of most any age. The dedicated interface unit processor(s) and corresponding memory allow the interface unit to be programmed to provide a number of functionalities that are not available in defibrillators that are commercially available today. Notably, given that the interface unit is a connected device that has a powerful processor (or processors) and a number of familiar I/O components including, for example, a touch sensitive display screen, Wi-Fi, cellular and other wireless communications capabilities, a speaker, a microphone and optionally a camera, the interface unit can be programmed to provide a number of useful functionalities without impacting the functionality of the base defibrillator unit in any way. Thus, it should be apparent that the described modular architecture helps overcome a number of practical challenges that have hindered widespread adoption of defibrillator connectivity.

Although only a few embodiments of the invention have been described in detail, it should be appreciated that the invention may be implemented in many other forms without departing from the spirit or scope of the invention. The described approach is particularly useful for public access AEDs. That is, AED that are placed in locations where they can be reached and used by the general public in emergencies. In such emergencies it is typically desirable to notify a PSAP (e.g., 911) so that emergency services (e.g. EMTs, paramedics, etc.) can be sent to professionally respond to the incident. This contrasts with AEDs that may be carried by medical professionals (e.g., EMTs, paramedics, etc.) or used in medical facilities such as hospitals where professional responders are typically already on site and notifying 911 may be undesirable.

The present embodiments should be considered illustrative and not restrictive, and the invention is not to be limited to the details given herein, but may be modified within the scope and equivalents of the appended claims.

What is claimed is:

1. A method comprising:

by a server, receiving a first electronic message from an automated external defibrillator (AED) in real-time during an emergency use of the AED, wherein the first message indicates one selected from the group consisting of (i) that the AED has performed a classification of a heart rhythm of the patient, and (ii) that the AED has determined that the patient has a shockable heart rhythm;

by the server, determining that an emergency services notification triggering event has occurred based at least in part on the reception of the first message that indicates the one selected from the group consisting of (i) that the AED has performed a classification of a heart rhythm of the patient, and (ii) that the AED has determined that the patient has a shockable heart rhythm; and in response to determining that an emergency services notification triggering event has occurred, sending an electronic incident notification message that either directly or indirectly causes an emergency services call center responsible for handling medical incidents in a region that includes the location of the AED to be notified of the emergency use of the AED, wherein the incident notification message includes an incident location indicative of the location of the AED; and wherein the server is located remotely relative to both the AED and the emergency services call center; and wherein the electronic incident notification message is sent during the emergency use of the AED.

2. A method comprising:

by a server, receiving a first electronic message from an automated external defibrillator (AED) during an emergency use of the AED;

by the server, receiving an indication of the AED's current location together with a location accuracy measure or location accuracy confidence value, wherein the location accuracy measure or location accuracy confidence value is received during the emergency use of the AED either in the first electronic message or a second electronic message from the AED;

by the server, determining whether the location of the AED is known within a designated location precision threshold based at least in part on the received location accuracy measure or location accuracy confidence value; and by the server, determining that an emergency services notification triggering event has occurred based at least in part on (a) the reception of the first message, and (b) the determination that the location of the AED is known within the designated location precision threshold; and in response to determining that an emergency services notification triggering event has occurred, sending an electronic incident notification message that directly or indirectly causes an emergency services call center responsible for handling medical incidents in a region that includes the location of the AED to be notified of the emergency use of the AED, wherein the incident notification message includes an incident location indicative of the location of the AED; and wherein the server is located remotely relative to both the AED and the emergency services call center; and wherein the electronic incident notification message is sent during the emergency use of the AED.

3. A method comprising:

by a server, receiving a first electronic message from an automated external defibrillator (AED) in real-time during an emergency use of the AED, wherein the first message indicates one selected from the group consisting of (i) that the AED has detected placement of the AED's electrode pads on a patient, (ii) that the AED has performed a classification of a heart rhythm of the patient, and (iii) that the AED has determined that the patient has a shockable heart rhythm;

by the server, receiving an indication of the AED's location together with a location accuracy measure or location accuracy confidence value, wherein the location accuracy measure or location accuracy confidence value is received during the emergency use of the AED either in the first electronic message or a second electronic message from the AED; and by the server, determining whether the location of the AED is known within a designated location precision threshold based at least in part on the received location accuracy measure or location accuracy confidence value;

by the server, determining that an emergency services notification triggering event has occurred based at least in part on the reception of the first message that indicates the one selected from the group consisting of (i) that the AED has detected placement of the AED's electrode pads on a patient or that the AED, (ii) that the AED has performed a classification of a heart rhythm of the patient, and (iii) that the AED has determined that the patient has a shockable heart rhythm, wherein the determination that an emergency services notification triggering event has occurred is further based at least in part on the determination that the location of the AED is known within the designated location precision threshold; and in response to determining that an emergency services notification triggering event has occurred, sending an electronic incident notification message that either directly or indirectly causes an emergency services call center responsible for handling medical incidents in a region that includes the location of the AED to be notified of the emergency use of the AED, wherein the incident notification message includes an incident location indicative of the location of the AED; and wherein the server is located remotely relative to both the AED and the emergency services call center; and wherein the electronic incident notification message is sent during the emergency use of the AED.

4. A method as recited in claim 3 wherein when it is determined that the location of the AED is not known within the designated location precision threshold, it is determined that an emergency services notification triggering event has not occurred and no electronic incident notification message is sent in response to reception of the first message.

5. A method as recited in claim 3 wherein the first message indicates that the AED has detected placement of the AED's electrode pads on the patient whereby the determination that the emergency services notification triggering event has occurred is based at least in part on the reception of the first message indicating that the AED has detected placement of the AED's electrode pads on a patient.

6. A method as recited in claim 1 wherein the first message indicates that the AED has performed a classification of a heart rhythm of the patient whereby the determination that the emergency services notification triggering event has occurred is based at least in part on the reception of the first message indicating that the AED has performed a classification of a heart rhythm of the patient.

7. A method as recited in claim 1 wherein the first message indicates that the AED has determined that the patient has a shockable heart rhythm whereby the determination that the emergency services notification triggering event has occurred is based at least in part on the reception of the first message indicating that the AED has determined that the patient has a shockable heart rhythm.

8. A method as recited in claim 2 wherein the incident notification message is sent directly from the server to a computer aided dispatch system used by the emergency services call center.

9. A method as recited in claim 2 wherein the incident notification message is sent to an emergency services interface that automatically sends a call center incident notification to a computer aided dispatch system used by the emergency services call center.

10. A method as recited in claim 4 wherein:

the server is configured to receive electronic messages from a multiplicity of AEDs and the server determines whether an emergency services notification triggering event has occurred for each incident for which the server receives an electronic message indicating that a selected one of the multiplicity of AEDs has one selected from the group consisting of (i) detected placement of the selected AED's electrode pads on an associated patient or that the AED, (ii) performed a classification of a heart rhythm of the associated patient, and (iii) determined that the associated patient has a shockable heart rhythm;

each time the server determines that an emergency services notification triggering event has occurred, the server sends a corresponding electronic incident notification message that causes a corresponding emergency services call center that is responsible for handling medical incidents in a corresponding region that includes a location of the selected AED to be notified of the emergency use of the selected AED.

11. A method as recited in claim 10 wherein when the server determines that the location of the selected AED is not known within the designated location precision threshold, it is determined that a no electronic incident notification message is sent.

12. A method as recited in claim 2 wherein when it is determined that the location of the AED is not known within the designated location precision threshold, it is determined that an emergency services notification triggering event has not occurred and no electronic incident notification message is sent in response to reception of the first message.

13. A method as recited in claim 1 further comprising:

by the server, electronically receiving an emergency services notifications settings command from a management platform user interface rendered on a computing device associated with an administrator associated with a first automated external defibrillator (AED), wherein the emergency services notifications settings command is received prior to the emergency use of the AED and indicates whether emergency uses of the AED should be reported to emergency services in real-time during emergency use of the AED; and in response to reception of the emergency services notifications command, marking a record in a first database associated with the server to indicate whether emergency services notifications are enabled or disabled for the AED; and wherein the determination of whether the emergency services notification triggering event has occurred is further based at least in part on whether emergency services notifications are enabled for the AED, and wherein it is determined that the emergency services notification triggering event has not occurred when emergency services notifications are disabled.

14. A method as recited in claim 2 wherein the emergency services call center is a public safety answering point (PSAP).

15. A method comprising:

by the server, electronically receiving an emergency services notifications settings command from a management platform user interface rendered on a computing device associated with an administrator associated with a first automated external defibrillator (AED), wherein the emergency services notifications settings command indicates whether emergency uses of the AED should be reported to emergency services in real-time during emergency use of the AED;

in response to reception of the emergency services notifications command, marking a record in a first database associated with the server to indicate whether emergency services notifications are enabled or disabled for the AED;

by a server, receiving a first electronic message from an automated external defibrillator (AED) during an emergency use of the AED; and by the server, determining whether an emergency services notification triggering event has occurred based at least in part on (a) whether emergency services notifications are enabled for the AED and (b) the reception of the first message; and in response to determining that an emergency services notification triggering event has occurred, sending an electronic incident notification message that directly or indirectly causes an emergency services call center responsible for handling medical incidents in a region that includes the location of the AED to be notified of the emergency use of the AED, wherein the incident notification message includes an incident location indicative of the location of the AED; and wherein the server is located remotely relative to both the AED and the emergency services call center; and wherein the electronic incident notification message is sent in during the emergency use of the AED.

16. A method comprising:

by a server, electronically receiving an emergency services notifications settings command from a management platform user interface rendered on a computing device associated with an administrator associated with a first automated external defibrillator (AED), wherein the emergency services notifications settings command indicates whether emergency uses of the AED should be reported to emergency services in real-time during emergency use of the AED;

in response to reception of the emergency services notifications command, marking a record in a first database associated with the server to indicate whether emergency services notifications are enabled or disabled for the AED;

by a server, receiving a first electronic message from an automated external defibrillator (AED) in real-time during an emergency use of the AED, wherein the first message directly or indirectly indicates that the AED is currently in use;

by the server, receiving an indication of the AED's location together with a location accuracy measure or location accuracy confidence value, wherein the location accuracy measure or location accuracy confidence value is received in real-time during the emergency use of the AED either in the first electronic message or a second electronic message from the AED;

by the server, determining whether the location of the AED is known within a designated location precision threshold based at least in part on the received location accuracy measure or location accuracy confidence value; and by the server, determining whether an emergency services notification triggering event has occurred based at least in part on (a) whether emergency services notifications are enabled for the AED, (b) the reception of the first message, and (c) the determination that the location of the AED is known within the designated location precision threshold; and in response to determining that an emergency services notification triggering event has occurred, sending an electronic incident notification message that causes an emergency services call center responsible for handling medical incidents in a region that includes the location of the AED to be notified of the emergency use of the AED, wherein the incident notification message includes an incident location indicative of the location of the AED; and wherein the server is located remotely relative to both the AED and the emergency services call center; and wherein the electronic incident notification message is sent during the emergency use of the AED.

17. A method as recited in claim 16 wherein when emergency services notifications are disabled for the AED it is determined that an emergency services notification triggering event has not occurred and no electronic incident notification message is sent in response to reception of the first message.

18. A method as recited in claim 16 wherein when it is determined that the location of the AED is not known within the designated location precision threshold, it is determined that an emergency services notification triggering event has not occurred and no electronic incident notification message is sent in response to reception of the first message.

19. A method as recited in claim 16 wherein the first message indicates that the AED has detected placement of the AED's electrode pads on the patient whereby the determination that the emergency services notification triggering event has occurred is based at least in part on the reception of the first message indicating that the AED has detected placement of the AED's electrode pads on a patient.

20. A method as recited in claim 16 wherein the first message indicates that the AED has performed a classification of a heart rhythm of the patient whereby the determination that the emergency services notification triggering event has occurred is based at least in part on the reception of the first message indicating that the AED has performed a classification of a heart rhythm of the patient.

21. A method as recited in claim 16 wherein the first message indicates that the AED has determined that the patient has a shockable heart rhythm whereby the determination that the emergency services notification triggering event has occurred is based at least in part on the reception of the first message indicating that the AED has determined that the patient has a shockable heart rhythm.

\* \* \* \* \*